United States Patent
Xue et al.

(10) Patent No.: US 6,642,255 B2
(45) Date of Patent: Nov. 4, 2003

(54) 1,2,-DISUBSTITUTED CYCLIC INHIBITORS OF MATRIX METALLOPROTEASES AND TNF-ALPHA

(75) Inventors: Chu-Biao Xue, Hockessin, DE (US); Carl Decicco, Kennett Square, PA (US); Xiaohua He, Hockessin, DE (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

(21) Appl. No.: 10/043,541

(22) Filed: Jan. 9, 2002

(65) Prior Publication Data

US 2003/0087890 A1 May 8, 2003

Related U.S. Application Data

(60) Provisional application No. 60/260,957, filed on Jan. 11, 2001.

(51) Int. Cl.[7] .............. A61K 31/47; C07D 215/16; C07D 215/38
(52) U.S. Cl. ............... 514/312; 546/156; 546/159
(58) Field of Search .................. 514/312; 546/156, 546/159

(56) References Cited

FOREIGN PATENT DOCUMENTS

| | | |
|---|---|---|
| EP | 780386 A | 6/1997 |
| EP | 818442 A | 1/1998 |
| WO | WO 9720824 A | 6/1997 |
| WO | WO 9732846 A | 9/1997 |
| WO | WO 9839316 A | 9/1998 |
| WO | WO 9958528 | 11/1999 |

*Primary Examiner*—D. Margaret Seaman
(74) *Attorney, Agent, or Firm*—David H Vance; Jing S. Belfield

(57) ABSTRACT

The present application describes novel 1,2-disubsituted cyclic derivatives of formula I:

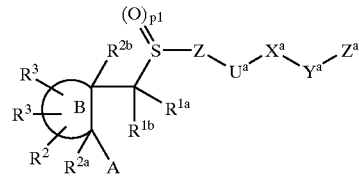

or pharmaceutically acceptable salt forms thereof, wherein ring B is a 3–8 membered non-aromatic ring consisting of: carbon atoms, 0–1 carbonyl groups, 0–1 double bonds, and from 0–2 ring heteroatoms selected from O, N, $NR^2$, and $S(O)p$ and the other variables are defined in the present specification, which are useful as metalloprotease and as TNF-α inhibitors.

30 Claims, No Drawings

1,2,-DISUBSTITUTED CYCLIC INHIBITORS OF MATRIX METALLOPROTEASES AND TNF-ALPHA

CROSS-REFERENCE TO RELATED APPLICATIONS

This application claims the benefit of U.S. Provisional App. Ser. No. 60/260,957, filed Jan. 11, 2001.

FIELD OF THE INVENTION

This invention relates generally to novel 1,2-disubstituted cyclic matrix metalloproteases and TNF-α inhibitors and pharmaceutical compositions containing the same and methods of using the same.

BACKGROUND OF THE INVENTION

There is now a body of evidence that metalloproteases (MP) are important in the uncontrolled breakdown of connective tissue, including proteoglycan and collagen, leading to resorption of the extracellular matrix. This is a feature of many pathological conditions, such as rheumatoid and osteoarthritis, corneal, epidermal or gastric ulceration; tumor metastasis or invasion; periodontal disease and bone disease. Normally these catabolic enzymes are tightly regulated at the level of their synthesis as well as at their level of extracellular activity through the action of specific inhibitors, such as alpha-2-macroglobulins and TIMPs (tissue inhibitors of metalloprotease), which form inactive complexes with the MP's.

Osteo- and Rheumatoid Arthritis (OA and RA respectively) are destructive diseases of articular cartilage characterized by localized erosion of the cartilage surface. Findings have shown that articular cartilage from the femoral heads of patients with OA, for example, had a reduced incorporation of radiolabeled sulfate over controls, suggesting that there must be an enhanced rate of cartilage degradation in OA (Mankin et al. J. Bone Joint Surg. 52A, 1970, 424–434). There are four classes of protein degradative enzymes in mammalian cells: serine, cysteine, aspartic and metalloproteases. The available evidence supports that it is the metalloproteases that are responsible for the degradation of the extracellular matrix of articular cartilage in OA and RA. Increased activities of collagenases and stromelysin have been found in OA cartilage and the activity correlates with severity of the lesion (Mankin et al. Arthritis Rheum. 21, 1978, 761–766, Woessner et al. Arthritis Rheum. 26, 1983, 63–68 and Ibid. 27, 1984, 305–312). In addition, aggrecanase has been identified as providing the specific cleavage product of proteoglycan found in RA and OA patients (Lohmander L. S. et al. Arthritis Rheum. 36, 1993, 1214–22).

Therefore, metalloproteases (MP) have been implicated as the key enzymes in the destruction of mammalian cartilage and bone. It can be expected that the pathogenesis of such diseases can be modified in a beneficial manner by the administration of MP inhibitors, and many compounds have been suggested for this purpose (see Wahl et al. Ann. Rep. Med. Chem. 25, 175–184, AP, San Diego, 1990).

Tumor necrosis factor (TNF) is a cell-associated cytokine that is processed from a 26 kd precursor form to a 17 kd active form. TNF has been shown to be a primary mediator in humans and in animals, of inflammation, fever, and acute phase responses, similar to those observed during acute infection and shock. Excess TNF has been shown to be lethal. There is now considerable evidence that blocking the effects of TNF with specific antibodies can be beneficial in a variety of circumstances including autoimmune diseases such as rheumatoid arthritis (Feldman et al, Lancet, 1994, 344, 1105) and non-insulin dependent diabetes melitus. (Lohmander L. S. et al. Arthritis Rheum. 36, 1993, 1214–22) and Crohn's disease (MacDonald T. et al. Clin. Exp. Immunol. 81, 1990, 301).

Compounds which inhibit the production of TNF are therefore of therapeutic importance for the treatment of inflammatory disorders. Recently it has been shown that a matrix metalloprotease or family of metalloproteases, hereafter known as TNF-convertases (TNF-C), as well as other MP's are capable of cleaving TNF from its inactive to active form (Gearing et al Nature, 1994, 370, 555). This invention describes molecules that inhibit this conversion and hence the secretion of active TNF-α from cells. These novel molecules provide a means of mechanism based therapeutic intervention for diseases including but not restricted to septic shock, haemodynamic shock, sepsis syndrome, post ischemic reperfusion injury, malaria, Crohn's disease, inflammatory bowel diseases, mycobacterial infection, meningitis, psoriasis, congestive heart failure, fibrotic diseases, cachexia, graft rejection, cancer, diseases involving angiogenesis, autoimmune diseases, skin inflammatory diseases, OA, RA, multiple sclerosis, radiation damage, hyperoxic alveolar injury, periodontal disease, HIV and non-insulin dependent diabetes melitus.

Since excessive TNF production has been noted in several disease conditions also characterized by MMP-mediated tissue degradation, compounds which inhibit both MMPs and TNF production may also have a particular advantage in diseases where both mechanisms are involved.

EP 0,780,286 describes MMP inhibitors of formula A:

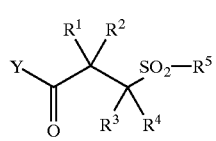

A wherein Y can be NHOH, $R^1$ and $R^2$ can combine to form a cycloalkyl or heterocycloalkyl group, $R^3$ and $R^4$ can be a variety of groups including H, and $R^5$ can be substituted aryl. Such compounds are not considered to be part of the present invention.

WO 97/20824 depicts MMP inhibitors of formula B:

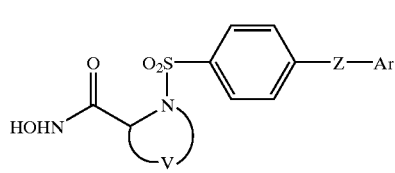

B wherein ring V contains six atoms, Z is O or S, and Ar is an aryl or heteroaryl group. Ar is preferably a monocyclic aryl group with an optional para substituent or an unsubstituted monocyclic heteroaryl group. Compounds of this sort are not considered to be part of the present invention.

EP 0,818,442 illustrates MMP inhibitors of formula C:

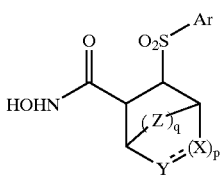

wherein Ar is optionally substituted phenyl or naphthyl, Z can be absent and X and Y can be a variety of substituents. Compounds like this are not considered to be part of the present invention.

WO 98/39316 presents MMP inhibitors of formula D:

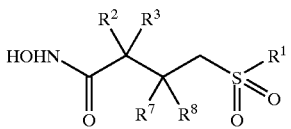

wherein $R^6$ and $R^7$ can combine to form a heterocycle and $R^1$ can be a substituted aryl group. These types of compounds are not considered to be part of the present invention.

WO 97/32846 describes MMP inhibitors of formula E:

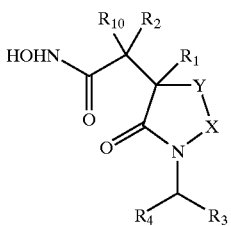

wherein $R_1$ can be a sulfonyl aryl group. Compounds of this sort are not considered to be part of the present invention.

The compounds of the present invention act as inhibitors of MPs, in particular aggrecanase and TNF-α. These novel molecules are provided as anti-inflammatory compounds and cartilage protecting therapeutics. The inhibition of aggrecanase, TNF-C, and other metalloproteases by molecules of the present invention indicates they are anti-inflammatory and should prevent the degradation of cartilage by these enzymes, thereby alleviating the pathological conditions of OA and RA.

SUMMARY OF THE INVENTION

Accordingly, one object of the present invention is to provide novel cyclic hydroxamic acids useful as metalloprotease inhibitors or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating inflammatory disorders, comprising: administering to a host, in need of such treatment, a therapeutically effective amount of at least one of the compounds of the present invention or a pharmaceutically acceptable salt or prodrug form thereof.

These and other objects, which will become apparent during the following detailed description, have been achieved by the inventors' discovery that compounds of formula (I):

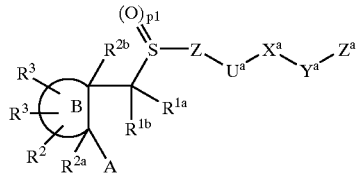

or pharmaceutically acceptable salt or prodrug forms thereof, wherein A, B, p1, $R^{1a}$, $R^{1b}$, $R^2$, $R^{2a}$, $R^{2b}$, $R^3$, $U^a$, $X^a$, $Y^a$, Z, and $Z^a$ are defined below, are effective metalloprotease inhibitors.

DETAILED DESCRIPTION OF PREFERRED EMBODIMENTS

[1] Thus, in an embodiment, the present invention provides a novel compound of formula I:

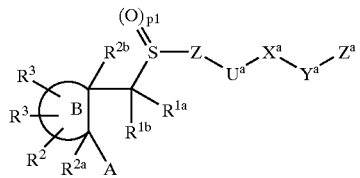

or a stereoisomer or pharmaceutically acceptable salt form thereof, wherein;

A is selected from —$COR^5$, —$CO_2H$, $CH_2CO_2H$, —$CO_2R^6$, —CONHOH, —$CONHOR^5$, —$CONHOR^6$, —N(OH)CHO, —N(OH)$COR^5$, —SH, —$CH_2SH$, —$SONHR^a$, —$SN_2H_2R^a$, —$PO(OH)_2$, and —PO(OH)$NHR^a$;

ring B is a 3–10 membered carbocyclic or heterocyclic ring consisting of: carbon atoms, 0–1 carbonyl groups, 0–3 double bonds, and from 0–2 ring heteroatoms selected from O, N, $NR^2$, and $S(O)_p$, provided that ring B contains other than a S—S, O—O, or S—O bond and provided that N—$R^2$ forms other than an N—O, N—N, or N—S bond;

Z is absent or selected from a $C_{3-13}$ carbocyclic residue substituted with 0–5 $R^b$ and a 5–14 membered heterocycle consisting of: carbon atoms and 1–4 heteroatoms selected from the group consisting of N, O, and $S(O)_p$ and substituted with 0–5 $R^b$;

$U^a$ is absent or is selected from: O, $NR^{a1}$, C(O), C(O)O, OC(O), C(O)$NR^{a1}$, $NR^{a1}$C(O), OC(O)O, OC(O)$NR^{a1}$, $NR^{a1}$C(O)O, $NR^{a1}$C(O)$NR^{a1}$, $S(O)_p$, $S(O)_p NR^{a1}$, $NR^{a1}S(O)_p$, and $NR^{a1}SO_2NR^{a1}$;

$X^a$ is absent or selected from $C_{1-10}$ alkylene, $C_{2-10}$ alkenylene, and $C_{2-10}$ alkynylene;

$Y^a$ is absent or selected from O, $NR^{a1}$, $S(O)_p$, and C(O);

$Z^a$ is selected from a $C_{3-13}$ carbocyclic residue substituted with 0–5 $R^c$ and a 5–14 membered heterocycle consisting of: carbon atoms and 1–4 heteroatoms selected from the group consisting of N, O, and $S(O)_p$ and substituted with 0–5 $R^c$;

provided that Z, $U^a$, $Y^a$, and $Z^a$ do not combine to form a N—N, N—O, O—N, O—O, $S(O)_p$—O, O—$S(O)_p$ or $S(O)_p$—$S(O)_p$ group;

$R^{1a}$ is selected from H, $C_{1-4}$ alkyl, phenyl, benzyl, $CH_2OR^3$, and $CH_2NR^aR^{a1}$;

$R^{1b}$ is selected from H, $C_{1-4}$ alkyl, phenyl, benzyl, $CH_2OR^3$, and $CH_2NR^aR^{a1}$;

alternatively, $R^{1a}$ and $R^{1b}$ combine to form a 3–6 membered ring consisting of: carbon atoms and 0–1 heteroatoms selected from O, $NR^a$, and $S(O)_p$;

$R^2$ is selected from Q, $C_{1-10}$ alkylene-Q substituted with 0–3 $R^{b1}$, $C_{2-10}$ alkenylene-Q substituted with 0–3 $R^{b1}$, $C_{2-10}$ alkynylene-Q substituted with 0–3 $R^{b1}$, $(CR^aR^{a1})_{r1}O(CR^aR^{a1})_r$—Q, $(CR^aR^{a1})_{r1}NR^a(CR^aR^{a1})_r$—Q, $(CR^aR^{a1})_{r1}C(O)(CR^aR^{a1})_r$—Q, $(CR^aR^{a1})_{r1}C(O)O(CR^aR^{a1})_r$—Q, $(CR^aR^{a1})_{r1}OC(O)(CR^aR^{a1})_r$—Q, $(CR^aR^{a1})_{r1}C(O)NR^aR^{a1}$, $(CR^aR^{a1})_{r1}C(O)NR^a(CR^aR^{a1})_r$—Q, $(CR^aR^{a1})_{r1}NR^aC(O)(CR^aR^{a1})_r$—Q, $(CR^aR^{a1})_{r1}OC(O)O(CR^aR^{a1})_r$—Q, $(CR^aR^{a1})_{r1}OC(O)NR^a(CR^aR^{a1})_r$—Q, $(CR^aR^{a1})_{r1}NR^aC(O)O(CR^aR^{a1})_r$—Q, $(CR^aR^{a1})_{r1}NR^aC(O)NR^a(CR^aR^{a1})_r$—Q, $(CR^aR^{a1})_{r1}S(O)_p(CR^aR^{a1})_r$—Q, $(CR^aR^{a1})_{r1}SO_2NR^a(CR^aR^{a1})_r$—Q, $(CR^aR^{a1})_{r1}NR^aSO_2(CR^aR^{a1})_r$—Q, and $(CR^aR^{a1})_{r1}NR^aSO_2NR^a(CR^aR^{a1})_r$—Q;

$R^{2a}$ is selected from H, $C_{1-6}$ alkyl, $OR^a$, $NR^aR^{a1}$, and $S(O)_pR^a$;

$R^{2b}$ is H or $C_{1-6}$ alkyl;

Q is selected from H, a $C_{3-13}$ carbocyclic residue substituted with 0–5 $R^d$ and a 5–14 membered heterocycle consisting of: carbon atoms and 1–4 heteroatoms selected from the group consisting of N, O, and $S(O)_p$ and substituted with 0–5 $R^d$;

$R^3$, at each occurrence, is selected from $Q^1$, $C_{1-6}$ alkylene-$Q^1$, $C_{2-6}$ alkenylene-$Q^1$, $C_{2-6}$ alkynylene-$Q^1$, $(CR^aR^{a1})_{r1}O(CH_2)_r$—$Q^1$, $(CR^aR^{a1})_{r1}NR^a(CR^aR^{a1})_r$—$Q^1$, $(CR^aR^{a1})_{r1}NR^aC(O)(CR^aR^{a1})_r$—$Q^1$, $(CR^aR^{a1})_{r1}C(O)NR^a(CR^aR^{a1})_r$—$Q^1$, $(CR^aR^{a1})_{r1}C(O)(CR^aR^{a1})_r$—$Q^1$, $(CR^aR^{a1})_{r1}C(O)O(CR^aR^{a1})_rQ^1$, $(CR^aR^{a1}_2)_{r1}S(O)_p(CR^aR^{a1})_r$—$Q^1$, and $(CR^aR^{a1})_{r1}SO_2NR^a(CR^aR^{a1})_r$—$Q^1$;

alternatively, when two $R^3$s are attached to the same carbon atom, they combine to form a 3–8 membered carbocyclic or heterocyclic ring consisting of: carbon atoms and 0–3 heteroatoms selected from the group consisting of N, O, and $S(O)_p$ and substituted with 0–3 $R^d$;

$Q^1$ is selected from H, phenyl substituted with 0–3 $R^d$, naphthyl substituted with 0–3 $R^d$ and a 5–10 membered heteroaryl consisting of: carbon atoms and 1–4 heteroatoms selected from the group consisting of N, O, and $S(O)_p$ and substituted with 0–3 $R^d$;

$R^a$, at each occurrence, is independently selected from H, $C_{1-4}$ alkyl, phenyl and benzyl;

$R^{a1}$, at each occurrence, is independently selected from H and $C_{1-4}$ alkyl;

alternatively, $R^a$ and $R^{a1}$ when attached to a nitrogen are taken together with the nitrogen to which they are attached to form a 5 or 6 membered ring comprising carbon atoms and from 0–1 additional heteroatoms selected from the group consisting of N, O, and $S(O)_p$;

$R^{a2}$, at each occurrence, is independently selected from $C_{1-4}$ alkyl, phenyl and benzyl;

$R^b$, at each occurrence, is independently selected from $C_{1-6}$ alkyl, $OR^a$, Cl, F, Br, I, =O, —CN, $NO_2$, $NR^aR^{a1}$, $C(O)R^a$, $C(O)OR^a$, $C(O)NR^aR^{a1}$, $R^aNC(O)NR^aR^{a1}$, $OC(O)NR^aR^{a1}$, $R^aNC(O)O$, $S(O)_2NR^aR^{a1}$, $NR^aS(O)_2R^{a2}$, $NR^aS(O)_2NR^aR^{a1}$, $OS(O)_2NR^aR^{a1}$, $NR^aS(O)_2R^{a2}$, $S(O)_pR^{a2}$, $CF_3$, and $CF_2CF_3$;

$R^{b1}$, at each occurrence, is independently selected from $OR^a$, Cl, F, Br, I, =O, —CN, $NO_2$, and $NR^aR^{a1}$;

$R^c$, at each occurrence, is independently selected from $C_{1-6}$ alkyl, $OR^a$, Cl, F, Br, I, =O, —CN, $NO_2$, $NR^aR^{a1}$, $C(O)R^a$, $C(O)OR^a$, $C(O)NR^aR^{a1}$, $R^aNC(O)NR^aR^{a1}$, $OC(O)NR^aR^{a1}$, $R^aNC(O)O$, $S(O)_2NR^aR^{a1}$, $NR^aS(O)_2R^{a2}$, $NR^aS(O)_2NR^aR^{a1}$, $OS(O)_2NR^aR^{a1}$, $NR^aS(O)_2R^{a2}$, $S(O)_pR^{a2}$, $CF_3$, $CF_2CF_3$, $C_{3-10}$ carbocyclic residue and a 5–14 membered heterocycle consisting of: carbon atoms and 1–4 heteroatoms selected from the group consisting of N, O, and $S(O)_p$;

$R^d$, at each occurrence, is independently selected from $C_{1-6}$ alkyl, $OR^a$, Cl, F, Br, I, =O, —CN, $NO_2$, $NR^aR^{a1}$, $C(O)R^a$, $C(O)OR^a$, $C(O)NR^aR^{a1}$, $R^aNC(O)NR^aR^{a1}$, $OC(O)NR^aR^{a1}$, $R^aNC(O)O$, $S(O)_2NR^aR^{a1}$, $NR^aS(O)_2R^{a2}$, $NR^aS(O)_2NR^aR^{a1}$, $OS(O)_2NR^aR^{a1}$, $NR^aS(O)_2R^{a2}$, $S(O)_pR^{a2}$, $CF_3$, $CF_2CF_3$, $C_{3-10}$ carbocyclic residue and a 5–14 membered heterocycle consisting of: carbon atoms and 1–4 heteroatoms selected from the group consisting of N, O, and $S(O)_p$;

$R^5$, at each occurrence, is selected from $C_{1-10}$ alkyl substituted with 0–2 $R^b$, and $C_{1-8}$ alkyl substituted with 0–2 $R^e$;

$R^e$, at each occurrence, is selected from phenyl substituted with 0–2 $R^b$ and biphenyl substituted with 0–2 $R^b$;

$R^6$, at each occurrence, is selected from phenyl, naphthyl, $C_{1-10}$ alkyl-phenyl-$C_{1-6}$ alkyl-, $C_{3-11}$ cycloalkyl, $C_{1-6}$ alkylcarbonyloxy-$C_{1-3}$ alkyl-, $C_{1-6}$ alkoxycarbonyloxy-$C_{1-3}$ alkyl-, $C_{2-10}$ alkoxycarbonyl, $C_{3-6}$ cycloalkylcarbonyloxy-$C_{1-3}$ alkyl-, $C_{3-6}$ cycloalkoxycarbonyloxy-$C_{1-3}$ alkyl-, $C_{3-6}$ cycloalkoxycarbonyl, phenoxycarbonyl, phenyloxycarbonyloxy-$C_{1-3}$ alkyl-, phenylcarbonyloxy-$C_{1-3}$ alkyl-, $C_{1-6}$ alkoxy-$C_{1-6}$ alkylcarbonyloxy-$C_{1-3}$ alkyl-, [5-($C_1$–$C_5$ alkyl)-1,3-dioxa-cyclopenten-2-one-yl]methyl, [5-($R^a$)-1,3-dioxa-cyclopenten-2-one-yl]methyl, (5-aryl-1,3-dioxa-cyclopenten-2-one-yl)methyl, —$C_{1-10}$ alkyl-$NR^7R^{7a}$, —$CH(R^8)OC(=O)R^9$, and —$CH(R^8)OC(=O)OR^9$;

$R^7$ is selected from H and $C_{1-10}$ alkyl, $C_{2-6}$ alkenyl, $C_{3-6}$ cycloalkyl-$C_{1-3}$ alkyl-, and phenyl-$C_{1-6}$ alkyl-;

$R^{7a}$ is selected from H and $C_{1-10}$ alkyl, $C_{2-6}$ alkenyl, $C_{3-6}$ cycloalkyl-$C_{1-3}$ alkyl-, and phenyl-$C_{1-6}$ alkyl-;

$R^8$ is selected from H and $C_{1-4}$ linear alkyl;

$R^9$ is selected from H, $C_{1-8}$ alkyl substituted with 1–2 $R^f$, $C_{3-8}$ cycloalkyl substituted with 1–2 $R^f$, and phenyl substituted with 0–2 $R^b$;

$R^f$, at each occurrence, is selected from $C_{1-4}$ alkyl, $C_{3-8}$ cycloalkyl, $C_{1-5}$ alkoxy, and phenyl substituted with 0–2 $R^b$;

p, at each occurrence, is selected from 0, 1, and 2;

p1 is 0, 1, or 2;

r, at each occurrence, is selected from 0, 1, 2, 3, and 4; and, r1, at each occurrence, is selected from 0, 1, 2, 3, and 4.

[2] In a preferred embodiment, the present invention provides a novel compound of formula II:

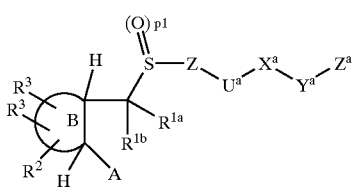

II or a stereoisomer or pharmaceutically acceptable salt form thereof, wherein;

A is selected from —$CO_2H$, $CH_2CO_2H$, —CONHOH, —$CONHOR^5$, —$CONHOR^6$, —N(OH)CHO, —N(OH)$COR^5$, —SH, and —$CH_2SH$;

ring B is a 4–7 membered carbocyclic or heterocyclic ring consisting of: carbon atoms, 0–1 carbonyl groups, 0–3 double bonds, and from 0–2 ring heteroatoms selected from O, N, and $NR^2$, provided that ring B contains other than an O—O, bond and provided that N—$R^2$ forms other than an N—O, N—N, or N—S bond;

Z is absent or selected from a $C_{3-6}$ carbocyclic residue substituted with 0–4 $R^b$ and a 5–6 membered heterocycle consisting of: carbon atoms and 1–4 heteroatoms selected from the group consisting of N, O, and $S(O)_p$ and substituted with 0–3 $R^b$;

$U^a$ is absent or is selected from: O, $NR^{a1}$, C(O), C(O)O, C(O)$NR^{a1}$, $NR^{a1}$C(O), $S(O)_p$, and $S(O)_pNR^{a1}$;

$X^a$ is absent or selected from $C_{1-4}$ alkylene, $C_{2-4}$ alkenylene, and $C_{2-4}$ alkynylene;

$Y^a$ is absent or selected from O and $NR^{a1}$;

$Z^a$ is selected from H, a $C_{3-10}$ carbocyclic residue substituted with 0–5 $R^c$ and a 5–10 membered heterocycle consisting of: carbon atoms and 1–4 heteroatoms selected from the group consisting of N, O, and $S(O)_p$ and substituted with 0–5 $R^c$;

provided that Z, $U^a$, $Y^a$, and $Z^a$ do not combine to form a N—N, N—O, O—N, O—O, $S(O)_p$—O, O—$S(O)_p$ or $S(O)_p$—$S(O)_p$ group;

$R^2$ is selected from Q, $C_{1-6}$ alkylene-Q, $C_{2-6}$ alkenylene-Q, $C_{2-6}$ alkynylene-Q, $(CR^aR^{a1})_{r1}O(CR^aR^{a1})_r$—Q, $(CR^aR^{a1})_{r1}NR^a(CR^aR^{a1})_r$—Q, $(CR^aR^{a1})_{r1}C(O)(CR^aR^{a1})_r$—Q, $(CR^aR^{a1})_{r1}C(O)O(CR^aR^{a1})_r$—Q, $(CR^aR^{a1})_rC(O)NR^aR^{a1}$, $(CR^aR^{a1})_{r1}C(O)NR^a(CR^aR^{a1})_r$—Q, $(CR^aR^{a1})_{r1}S(O)_p(CR^aR^{a1})_r$—Q, and $(CR^aR^{a1})_{r1}SO_2NR^a(CR^aR^{a1})_r$—Q;

Q is selected from H, a $C_{3-6}$ carbocyclic residue substituted with 0–5 $R^d$, and a 5–10 membered heterocycle consisting of: carbon atoms and 1–4 heteroatoms selected from the group consisting of N, O, and $S(O)_p$ and substituted with 0–5 $R^d$;

$R^a$, at each occurrence, is independently selected from H, $C_{1-4}$ alkyl, phenyl and benzyl;

$R^{a1}$, at each occurrence, is independently selected from H and $C_{1-4}$ alkyl;

alternatively, $R^a$ and $R^{a1}$ when attached to a nitrogen are taken together with the nitrogen to which they are attached to form a 5 or 6 membered ring comprising carbon atoms and from 0–1 additional heteroatoms selected from the group consisting of N, O, and $S(O)_p$;

$R^{a2}$, at each occurrence, is independently selected from $C_{1-4}$ alkyl, phenyl and benzyl;

$R^b$, at each occurrence, is independently selected from $C_{1-6}$ alkyl, $OR^a$, Cl, F, Br, =O, —CN, $NR^aR^{a1}$, C(O)$R^a$, C(O)$OR^a$, C(O)$NR^aR^{a1}$, $S(O)_2NR^aR^{a1}$, $S(O)_pR^{a2}$, and $CF_3$;

$R^c$, at each occurrence, is independently selected from $C_{1-6}$ alkyl, $OR^a$, Cl, F, Br, =O, —CN, $NR^aR^{a1}$, C(O)$R^a$, C(O)$OR^a$, C(O)$NR^aR^{a1}$, $S(O)_2NR^aR^{a1}$, $S(O)_pR^{a2}$, $CF_3$, $C_{3-6}$ carbocyclic residue and a 5–6 membered heterocycle consisting of: carbon atoms and 1–4 heteroatoms selected from the group consisting of N, O, and $S(O)_p$;

$R^d$, at each occurrence, is independently selected from $C_{1-6}$ alkyl, $OR^a$, Cl, F, Br, =O, —CN, $NR^aR^{a1}$, C(O)$R^a$, C(O)$OR^a$, C(O)$NR^aR^{a1}$, $S(O)_2NR^aR^{a1}$, $S(O)_pR^{a2}$, $CF_3$, $C_{3-6}$ carbocyclic residue and a 5–6 membered heterocycle consisting of: carbon atoms and 1–4 heteroatoms selected from the group consisting of N, O, and $S(O)_p$;

$R^5$, at each occurrence, is selected from $C_{1-6}$ alkyl substituted with 0–2 $R^b$, and $C_{1-4}$ alkyl substituted with 0–2 $R^e$;

$R^e$, at each occurrence, is selected from phenyl substituted with 0–2 $R^b$ and biphenyl substituted with 0–2 $R^b$;

$R^6$, at each occurrence, is selected from phenyl, naphthyl, $C_{1-10}$ alkyl-phenyl-$C_{1-6}$ alkyl-, $C_{3-11}$ cycloalkyl, $C_{1-6}$ alkylcarbonyloxy-$C_{1-3}$ alkyl-, $C_{1-6}$ alkoxycarbonyloxy-$C_{1-3}$ alkyl-, $C_{2-10}$ alkoxycarbonyl, $C_{3-6}$ cycloalkylcarbonyloxy-$C_{1-3}$ alkyl-, $C_{3-6}$ cycloalkoxycarbonyloxy-$C_{1-3}$ alkyl-, $C_{3-6}$ cycloalkoxycarbonyl, phenoxycarbonyl, phenyloxycarbonyloxy-$C_{1-3}$ alkyl-, phenylcarbonyloxy-$C_{1-3}$ alkyl-, $C_{1-6}$ alkoxy-$C_{1-6}$ alkylcarbonyloxy-$C_{1-3}$ alkyl-, [5-($C_1$–$C_5$ alkyl)-1,3-dioxa-cyclopenten-2-one-yl]methyl, [5-($R^a$)-1,3-dioxa-cyclopenten-2-one-yl]methyl, (5-aryl-1,3-dioxa-cyclopenten-2-one-yl)methyl, —$C_{1-10}$ alkyl-$NR^7R^{7a}$, —CH($R^8$)OC(=O)$R^9$, and —CH($R^8$)OC(=O)$OR^9$;

$R^7$ is selected from H and $C_{1-6}$ alkyl, $C_{2-6}$ alkenyl, $C_{3-6}$ cycloalkyl-$C_{1-3}$ alkyl-, and phenyl-$C_{1-6}$ alkyl-;

$R^{7a}$ is selected from H and $C_{1-6}$ alkyl, $C_{2-6}$ alkenyl, $C_{3-6}$ cycloalkyl-$C_{1-3}$ alkyl-, and phenyl-$C_{1-6}$ alkyl-;

$R^8$ is selected from H and $C_{1-4}$ linear alkyl;

$R^9$ is selected from H, $C_{1-6}$ alkyl substituted with 1–2 $R^f$, $C_{3-6}$ cycloalkyl substituted with 1–2 $R^f$, and phenyl substituted with 0–2 $R^b$;

$R^f$, at each occurrence, is selected from $CH_{1-4}$ alkyl; $C_{3-6}$ cycloalkyl, $C_{1-5}$ alkoxy, and phenyl substituted with 0–2 $R^b$;

p, at each occurrence, is selected from 0, 1, and 2;

r, at each occurrence, is selected from 0, 1, 2, 3, and 4; and, r1, at each occurrence, is selected from 0, 1, 2, 3, and 4.

[3] In a more preferred embodiment, the present invention provides a novel compound of formula III:

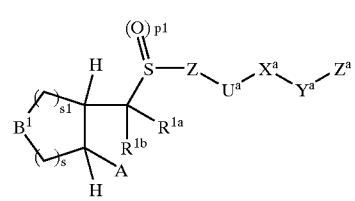

III or a stereoisomer or pharmaceutically acceptable salt form thereof, wherein;

A is selected from —$CO_2H$, $CH_2CO_2H$, —CONHOH, —$CONHOR^5$, —N(OH)CHO, and —N(OH)$COR^5$;

$B^1$ is selected from $NR^2$, O, and $CHR^2$, provided that N—$R^2$ forms other than an N—O, N—N, or N—S bond;

Z is absent or selected from a $C_{5-6}$ carbocyclic residue substituted with 0–3 $R^b$ and a 5–6 membered heteroaryl comprising carbon atoms and from 1–4 heteroatoms selected from the group consisting of N, O, and $S(O)_p$ and substituted with 0–3 $R^b$;

$U^a$ is absent or is selected from: O, $NR^{a1}$, C(O), C(O)$NR^{a1}$, $S(O)_p$, and $S(O)_pNR^{a1}$;

$X^a$ is absent or selected from $C_{1-2}$ alkylene and $C_{2-4}$ alkynylene;

$Y^a$ is absent or selected from O and $NR^{a1}$;

$Z^a$ is selected from H, a $C_{5-6}$ carbocyclic residue substituted with 0–3 $R^c$ and a 5–10 membered heteroaryl comprising carbon atoms and from 1–4 heteroatoms selected from the group consisting of N, O, and $S(O)_p$ and substituted with 0–3 $R^c$;

provided that z, $U^a$, $Y^a$, and $Z^a$ do not combine to form a N—N, N—O, O—N, O—O, $S(O)_p$—O, O—$S(O)_p$ or $S(O)_p$—$S(O)_p$ group;

$R^2$ is selected from Q, $C_{1-6}$ alkylene-Q, $C_{2-6}$ alkenylene-Q, $C_{2-6}$ alkynylene-Q, $(CR^aR^{a1})_{r1}O(CR^aR^{a1})_r$—Q, $(CR^aR^{a1})_{r1}NR^a(CR^aR^{a1})_r$—Q, $(CR^aR^{a1})_{r1}C(O)(CR^aR^{a1})_r$—Q, $(CR^aR^{a1})_{r1}C(O)O(CR^aR^{a1})_r$—Q, $(CR^aR^{a2})_{r1}C(O)NR^aR^{a1}$, $(CR^aR^{a2})_{r1}C(O)NR^a(CR^aR^{a1})_r$—Q, and $(CR^aR^{a1})_{r1}S(O)_p(CR^aR^{a1})_r$—Q;

Q is selected from H, a $C_{3-6}$ carbocyclic residue substituted with 0–3 $R^d$ and a 5–10 membered heterocycle consisting of: carbon atoms and 1–4 heteroatoms selected from the group consisting of N, O, and $S(O)_p$ and substituted with 0–3 $R^d$;

$R^a$, at each occurrence, is independently selected from H, $C_{1-4}$ alkyl, phenyl and benzyl;

$R^{a1}$, at each occurrence, is independently selected from H and $C_{1-4}$ alkyl;

$R^{a2}$, at each occurrence, is independently selected from $C_{1-4}$ alkyl, phenyl and benzyl;

$R^b$, at each occurrence, is independently selected from $C_{1-4}$ alkyl, $OR^a$, Cl, F, =O, $NR^aR^{a1}$, $C(O)R^a$, $C(O)OR^a$, $C(O)NR^aR^{a1}$, $S(O)_2NR^aR^{a1}$, $S(O)_pR^{a2}$, and $CF_3$;

$R^c$, at each occurrence, is independently selected from $C_{1-6}$ alkyl, $OR^a$, Cl, F, Br, =O, $NR^aR^{a1}$, $C(O)R^a$, $C(O)NR^aR^{a1}$, $S(O)_2NR^aR^{a1}$, $S(O)_pR^{a2}$, and $CF_3$;

$R^d$, at each occurrence, is independently selected from $C_{1-6}$ alkyl, $OR^a$, Cl, F, Br, =O, $NR^aR^{a1}$, $C(O)R^a$, $C(O)NR^aR^{a1}$, $S(O)_2NR^aR^{a1}$, $S(O)_pR^{a2}$, $CF_3$ and phenyl;

$R^5$, at each occurrence, is selected from $C_{1-4}$ alkyl substituted with 0–2 $R^b$, and $C_{1-4}$ alkyl substituted with 0–2 $R^e$;

$R^e$, at each occurrence, is selected from phenyl substituted with 0–2 $R^b$ and biphenyl substituted with 0–2 $R^b$;

p, at each occurrence, is selected from 0, 1, and 2;

r, at each occurrence, is selected from 0, 1, 2, 3, and 4;

r1, at each occurrence, is selected from 0, 1, 2, 3, and 4; and, s and s1 combine to total 1, 2, 3, or 4.

[4] In an even more preferred embodiment, the present invention provides a novel compound of formula IV:

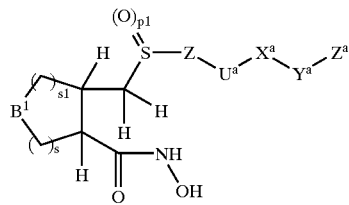

IV or a stereoisomer or pharmaceutically acceptable salt form thereof, wherein;

Z is absent or selected from phenyl substituted with 0–3 $R^b$ and pyridyl substituted with 0–3 $R^b$;

$U^a$ is absent or is O;

$X^a$ is absent or is selected from $CH_2$, $CH_2CH_2$, and $C_{2-4}$ alkynylene;

$Y^a$ is absent or is O;

$Z^a$ is selected from H, phenyl substituted with 0–3 $R^c$, pyridyl substituted with 0–3 $R^c$, and quinolinyl substituted with 0–3 $R^c$;

provided that Z, $U^a$, $Y^a$, and $Z^a$ do not combine to form a N—N, N—O, O—N, or O—O group;

$R^2$ is selected from Q, $C_{1-6}$ alkylene-Q, $C_{2-6}$ alkynylene-Q, $(CR^aR^{a1})_{r1}O(CR^aR^{a1})_r$—Q, $(CR^aR^{a1})_{r1}NR^a(CR^aR^{a1})_r$—Q, C(O) $(CR^aR^{a1})_r$—Q, $C(O)O(CR^aR^{a1})_r$—Q, $C(O)NR^a(CR^aR^{a1})_r$—Q, and $S(O)_p(CR^aR^{a1})_r$—Q;

Q is selected from H, cyclopropyl substituted with 0–1 $R^d$, cyclobutyl substituted with 0–1 $R^d$, cyclopentyl substituted with 0–1 $R^d$, cyclohexyl substituted with 0–1 $R^d$, phenyl substituted with 0–2 $R^d$ and a heteroaryl substituted with 0–3 $R^d$, wherein the heteroaryl is selected from pyridyl, quinolinyl, thiazolyl, furanyl, imidazolyl, and isoxazolyl;

$R^a$, at each occurrence, is independently selected from H, $CH_3$, and $CH_2CH_3$;

$R^{a1}$, at each occurrence, is independently selected from H, $CH_3$, and $CH_2CH_3$;

$R^{a2}$, at each occurrence, is independently selected from H, $CH_3$, and $CH_2CH_3$;

$R^b$, at each occurrence, is independently selected from $C_{1-4}$ alkyl, $OR^a$, Cl, F, =O, $NR^aR^{a1}$, $C(O)R^a$, $C(Q)OR^a$, $C(O)NR^aR^{a1}$, $S(O)_2NR^aR^{a1}$, $S(O)_pR^{a2}$, and $CF_3$;

$R^c$, at each occurrence, is independently selected from $C_{1-6}$ alkyl, $OR^a$, Cl, F, Br, =O, $NR^aR^{a1}$, $C(O)R^a$, $C(O)NR^aR^{a1}$, $S(O)_2NR^aR^{a1}$, $S(O)_pR^{a2}$, and $CF_3$;

$R^d$, at each occurrence, is independently selected from $C_{1-6}$ alkyl, $OR^a$, Cl, F, Br, =O, $NR^aR^{a1}$, $C(O)R^a$, $C(O)NR^aR^{a1}$, $S(O)_2NR^aR^{a1}$, $S(O)_pR^{a2}$, $CF_3$ and phenyl;

p, at each occurrence, is selected from 0, 1, and 2;

r, at each occurrence, is selected from 0, 1, 2, and 3;

r1, at each occurrence, is selected from 0, 1, 2, and 3; and, s and s1 combine to total 2, 3, or 4.

[5] In another preferred embodiment, the present invention provides a novel compound selected from the group:

(3R,4S)-N-hydroxy-1-methyl-3-[({4-[(2-methyl-4-quinolinyl)methoxy]phenyl}sulfonyl)methyl]-4-piperidinecarboxamide;

(3R,4S)-N-hydroxy-1-isopropyl-3-[({4-[(2-methyl-4-quinolinyl)methoxy]phenyl}sulfonyl)methyl]-4-piperidinecarboxamide;

tert-butyl (3S,4S)-4-[(hydroxyamino)carbonyl]-3-[({4-[(2-methyl-4-quinolinyl)methoxy]phenyl}sulfonyl)methyl]-1-piperidinecarboxylate;

(3S, 4S)-N-hydroxy-3-[({4-[(2-methyl-4-quinolinyl)methoxy]phenyl}sulfonyl)methyl]-4-piperidinecarboxamide;

(3S,4S)-N-hydroxy-1-methyl-3-[({4-[(2-methyl-4-quinolinyl)methoxy]phenyl}sulfonyl)methyl]-4-piperidinecarboxamide;

(3S, 4S)-N-hydroxy-1-isopropyl-3-[({4-[(2-methyl-4-quinolinyl)methoxy]phenyl}sulfonyl)methyl]-4-piperidinecarboxamide;

(3S,4S)-N-hydroxy-3-[({4-[(2-methyl-4-quinolinyl)methoxy]phenyl}sulfonyl)methyl]-1-propyl-4-piperidinecarboxamide;

(3S, 4S)-1-butyl-N-hydroxy-3-[({4-[(2-methyl-4-quinolinyl)methoxy]phenyl}sulfonyl)methyl]-4-piperidinecarboxamide;

(3S,4S)-N-hydroxy-1-isobutyl-3-[({4-[(2-methyl-4-quinolinyl)methoxy]phenyl}sulfonyl)methyl]-4-piperidinecarboxamide;

(3S,4S)-N-hydroxy-3-[({4-[(2-methyl-4-quinolinyl)methoxy]phenyl}sulfonyl)methyl]-1-(2-propynyl)-4-piperidinecarboxamide;

(3S,4S)-1-allyl-N-hydroxy-3-[({4-[(2-methyl-4-quinolinyl)methoxy]phenyl}sulfonyl)methyl]-4-piperidinecarboxamide;

tert-butyl (3R,4R)-3-[(hydroxyamino)carbonyl]-4-[({4-[(2-methyl-4-quinolinyl)methoxy]phenyl}sulfonyl)methyl]-1-piperidinecarboxylate;

(3R, 4R)-N-hydroxy-4-[({4-[(2-methyl-4-quinolinyl)methoxy]phenyl}sulfonyl)methyl]-3-piperidinecarboxamide;

(3R,4R)-N-hydroxy-1-methyl-4-[({4-[(2-methyl-4-quinolinyl)methoxy]phenyl}sulfonyl)methyl]-3-piperidinecarboxamide;

(3R,4R)-N-hydroxy-1-isopropyl-4-[({4-[(2-methyl-4-quinolinyl)methoxy]phenyl}sulfonyl)methyl]-3-piperidinecarboxamide;

(2S,3S)-N-hydroxy-2-[({4-[(2-methyl-4-quinolinyl)methoxy]phenyl}sulfonyl)methyl]-3-piperidinecarboxamide;

(2S,3S)-N-hydroxy-1-methyl-2-[({4-[(2-methyl-4-quinolinyl)methoxy]phenyl}sulfonyl)methyl]-3-piperidinecarboxamide;

(2R, 3S)-N-hydroxy-2-[({4-[(2-methyl-4-quinolinyl)methoxy]phenyl}sulfonyl)methyl]-3-piperidinecarboxamide;

(2R, 3S)-N-hydroxy-1-methyl-2-[({4-[(2-methyl-4-quinolinyl)methoxy]phenyl}sulfonyl)methyl]-3-piperidinecarboxamide;

(2R,3S)-N-hydroxy-2-[({4-[(2-methyl-4-quinolinyl)methoxy]phenyl}sulfonyl)methyl]-3-pyrrolidinecarboxamide;

(2R,3S)-N-hydroxy-1-methyl-2-[({4-[(2-methyl-4-quinolinyl)methoxy]phenyl}sulfonyl)methyl]-3-pyrrolidinecarboxamide;

tert-butyl (3R,4S)-3-[(hydroxyamino)carbonyl]-4-[({4-[(2-methyl-4-quinolinyl)methoxy]phenyl}sulfonyl)methyl]-1-pyrrolidinecarboxylate;

(3R,4S)-N-hydroxy-4-[({4-[(2-methyl-4-quinolinyl)methoxy]phenyl}sulfonyl)methyl]-3-pyrrolidinecarboxamide;

(3R,4S)-N-hydroxy-1-isopropyl-4-[({4-[(2-methyl-4-quinolinyl)methoxy]phenyl}sulfonyl)methyl]-3-pyrrolidinecarboxamide;

(3R,4S)-N-hydroxy-4-[({4-[(2-methyl-4-quinolinyl)methoxy]phenyl}sulfonyl)methyl]-1-(2-propynyl)-3-pyrrolidinecarboxamide;

(3S,4S)-N-hydroxy-3-({[4-(3-methoxyphenoxy)phenyl]sulfonyl}methyl)-4-piperidinecarboxamide;

(3S,4S)-3-({[4-(3-chlorophenoxy)phenyl]sulfonyl}methyl)-N-hydroxy-4-piperidinecarboxamide;

(3S, 4S)-N-hydroxy-3-({[4-(3-methylphenoxy)phenyl]sulfonyl}methyl)-4-piperidinecarboxamide;

(2R,3S)-N-hydroxy-1-isopropyl-2-[({4-[(2-methyl-4-quinolinyl)methoxy]phenyl}sulfonyl)methyl]-3-pyrrolidinecarboxamide;

(2R, 3S)-N-hydroxy-2-[({4-[(2-methyl-4-quinolinyl)methoxy]phenyl}sulfonyl)methyl]-1-(methylsulfonyl)-3-pyrrolidinecarboxamide;

(2R,3S)-1-(2-furoyl)-N-hydroxy-2-[({4-[(2-methyl-4-quinolinyl)methoxy]phenyl}sulfonyl)methyl]-3-pyrrolidinecarboxamide;

(2R,3S)-1-(3-furoyl)-N-hydroxy-2-[({4-[(2-methyl-4-quinolinyl)methoxy]phenyl}sulfonyl)methyl]-3-pyrrolidinecarboxamide;

(2R,3S)-N-hydroxy-2-[({4-[(2-methyl-4-quinolinyl)methoxy]phenyl}sulfonyl)methyl]-1-(tetrahydro-2-furanylcarbonyl)-3-pyrrolidinecarboxamide;

(2R,3S)-N-hydroxy-2-[({4-[(2-methyl-4-quinolinyl)methoxy]phenyl}sulfonyl)methyl]-1-(tetrahydro-3-furanylcarbonyl)-3-pyrrolidinecarboxamide; and, (2R,3S)-1-acetyl-N-hydroxy-2-[({4-[(2-methyl-4-quinolinyl)methoxy]phenyl}sulfonyl)methyl]-3-pyrrolidinecarboxamide;

or a pharmaceutically acceptable salt form thereof.

In another embodiment, the present invention provides a novel pharmaceutical composition, comprising: a pharmaceutically acceptable carrier and a therapeutically effective amount of a compound of formula I or a pharmaceutically acceptable salt form thereof.

In another embodiment, the present invention provides a novel method for treating an inflammatory disorder, comprising: administering to a patient in need thereof a therapeutically effective amount of a compound of the present invention or a pharmaceutically acceptable salt form thereof.

In another embodiment, the present invention provides a novel method, comprising: administering a compound of the present invention or a pharmaceutically acceptable salt form thereof in an amount effective to treat an inflammatory disorder.

In another embodiment, the present invention provides a novel method of treating a condition or disease mediated by MMPs, TNF, aggrecanase, or a combination thereof in a mammal, comprising: administering to the mammal in need of such treatment a therapeutically effective amount of a compound of formula I or a pharmaceutically acceptable salt form thereof.

In another embodiment, the present invention provides a novel method of treating, wherein the disease or condition is referred to as acute infection, acute phase response, age related macular degeneration, alcoholism, allergy, allergic asthma, aneurism, anorexia, aortic aneurism, asthma, athersclerosis, atopic dermatitis, autoimmune disease, autoimmune hepatitis, Bechet's disease, cachexia, calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pulmonary emphysema, pydoderma gangrenosum, relapsing polychondritis, Reiter's syndrome, rheumatic fever, rheumatoid arthritis, sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is intended to be taken individually as its own independent preferred embodiment. Furthermore, any element of an embodiment is meant to be combined with any and all other elements from any embodiment to describe an additional embodiment.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Geometric isomers of double bonds such as olefins and C=N double bonds can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^b$) occurs more than one time in any constituent or formula for a compound, its definition at each occurrence is independent of its definition at every other occurrence. Thus, for example, if a group is shown to be substituted with 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" is intended to include both branched and straight-chain saturated aliphatic hydrocarbon groups having the specified number of carbon atoms. $C_{1-10}$ alkyl (or alkylene), is intended to include $C_1$, $C_2$, $C_3$, $C_4$, $C_5$, $C_6$, $C_7$, $C_8$, $C_9$, and $C_{10}$ alkyl groups. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. $C_{1-10}$ alkoxy, is intended to include $C_1$, $C_2$, $C_3$, $C_4$, $C_5$, $C_6$, $C_7$, $C_8$, $C_9$, and $C_{10}$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. $C_{3-7}$ cycloalkyl, is intended to include $C_3$, $C_4$, $C_5$, $C_6$, and $C_7$ cycloalkyl groups. "Alkenyl" or "alkenylene" is intended to include hydrocarbon chains of either a straight or branched configuration and one or more unsaturated carbon—carbon bonds which may occur in any stable point along the chain, such as ethenyl and propenyl. $C_{2-10}$ alkenyl (or alkenylene), is intended to include $C_2$, $C_3$, $C_4$, $C_5$, $C_6$, $C_7$, $C_8$, $C_9$, and $C_{10}$ alkenyl groups. "Alkynyl" or "alkynylene" is intended to include hydrocarbon chains of either a straight or branched configuration and one or more triple carbon—carbon bonds which may occur in any stable point along the chain, such as ethynyl and propynyl. $C_{2-10}$ alkynyl (or alkynylene), is intended to include $C_2$, $C_3$, $C_4$, $C_5$, $C_6$, $C_7$, $C_8$, $C_9$, and $C_{10}$ alkynyl groups.

"Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2] bicyclooctane, fluorenyl, phenyl, naphthyl, indanyl, adamantyl, and tetrahydronaphthyl.

As used herein, the term "heterocycle" or "heterocyclic group" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic group" or "heteroaryl" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heterotams independently selected from the group consisting of N, NH, O and S. It is to be noted that total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc . . . ) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention or an amount of the combination of compounds claimed effective to inhibit a desired metalloprotease in a host. The combination of compounds is preferably a synergistic combination. Synergy, as described for example by Chou and Talalay, Adv. Enzyme Regul. 22:27–55 (1984), occurs when the effect (in this case, inhibition of the desired target) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased anti-inflammatory effect, or some other beneficial effect of the combination compared with the individual components.

SYNTHESIS

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment, and work up procedure, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used.

Compounds of formula I where A is a hydroxamic acid can be prepared using the methods described in Schemes 1–4. In Scheme 1, an alcohol 1 is converted to a halide or sulfonate 2. Displacement of 2 with a thiol using a base such as NaH produces the sulfide 3. Oxidation using an oxidant such as Oxone® gives rise to a sulfone derivative 4. Removal of the tert-butyl followed by coupling with hydroxylamine using a coupling agent such as BOP affords the hydroxamic acid 5 (Scheme 1).

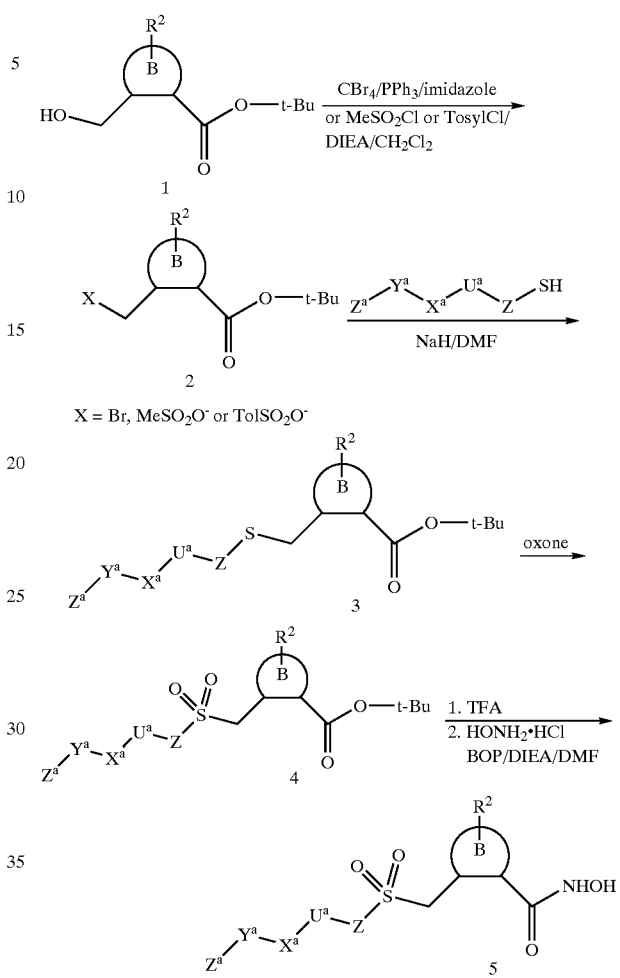

Alternatively, compound 5 can be prepared from a lactone 6 (Scheme 2). Ring opening of lactone 6 with a thiol using a base such as sodium hydride gives rise to an acid 7. Oxidation using an oxidant such as Oxone® produces a sulfone derivative 8. Coupling of 8 with hydroxylamine using a coupling agent such as BOP affords the hydroxamic acid 5.

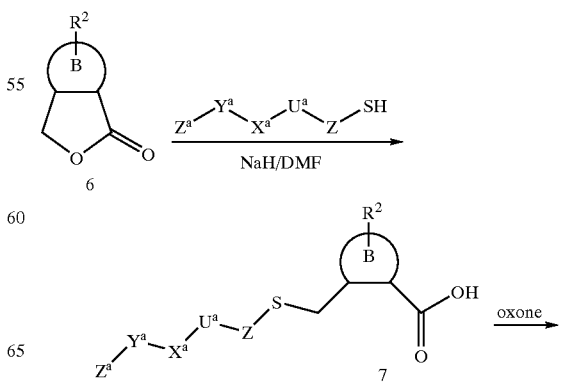

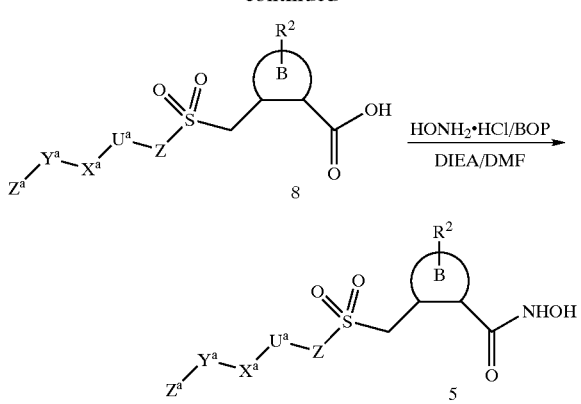

Intermediate 2 can be reacted with 4-mercaptophenol using a base such as sodium hydride to give the sulfide intermediate 9. Compound 9 can also be prepared from the lactone 6 by ring opening with 4-mercaptophenol followed by esterification with $XR^{11}$. Thioether 9 can be used as a common intermediate for derivatization at the phenol moiety. Alkylation of 9 with $ArCH_2X$ using a base provides the intermediate 10a. A copper (II) reaction of 9 with an aryl boronic acid gives rise to a biphenylether 10b. Treatment of 9 with triflic anhydride followed by a Suzuki reaction with an aryl boronic acid produces the biphenyl intermediate 10c. The intermediates 10a–10c where $R^{11}$ is a tert-butyl group are then converted to hydroxamic acids following the procedures described in Scheme 1.

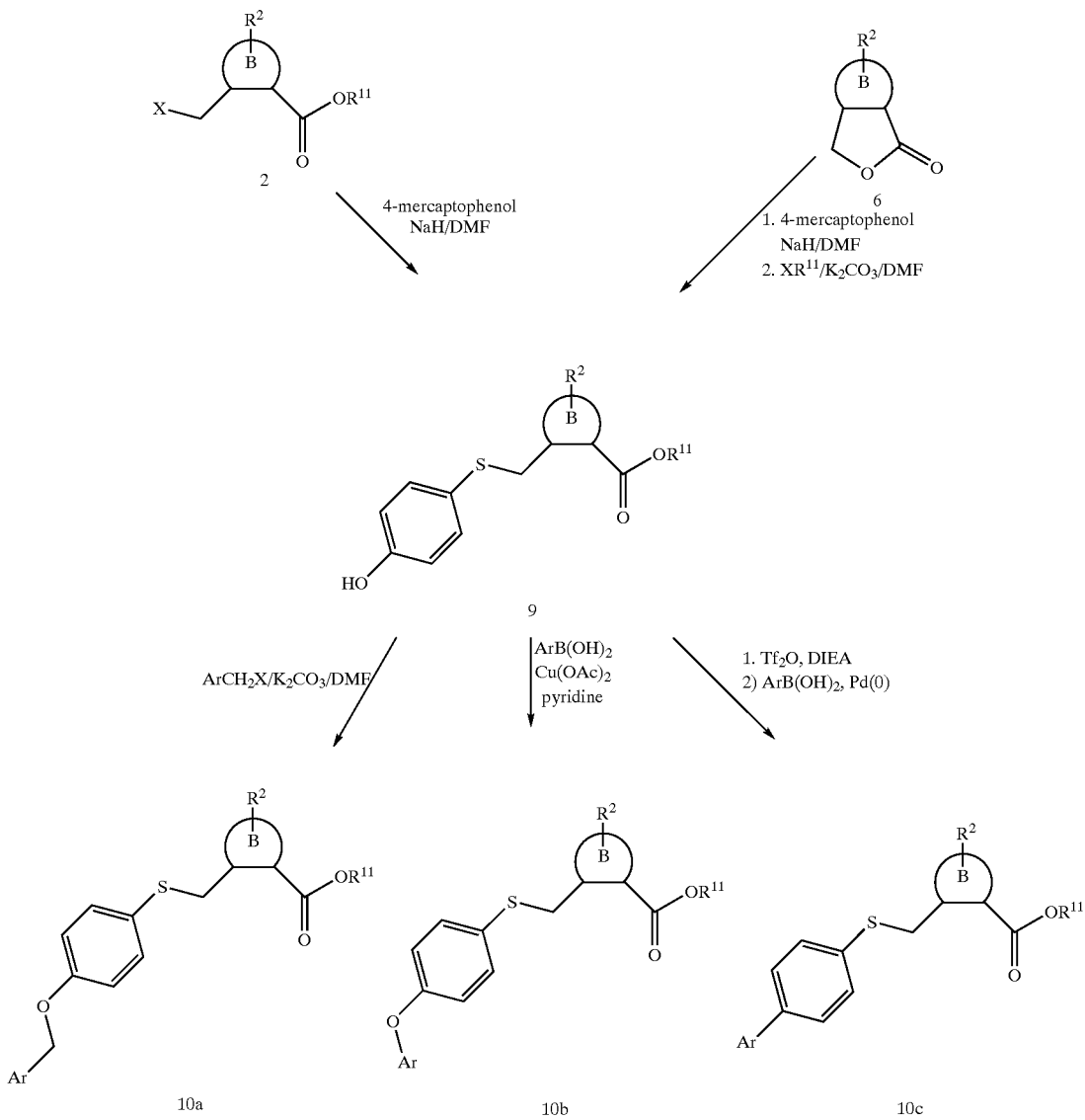

Scheme 3

When $R^{11}$ is a methyl group in intermediate 10, methyl ester 11 is subjected to an oxidation using an oxidant such as Oxone® to give a sulfone derivative 12. Treatment of 12 with a hydroxylamine solution in methanol provides the hydroxamic acid 13 (Scheme 4).

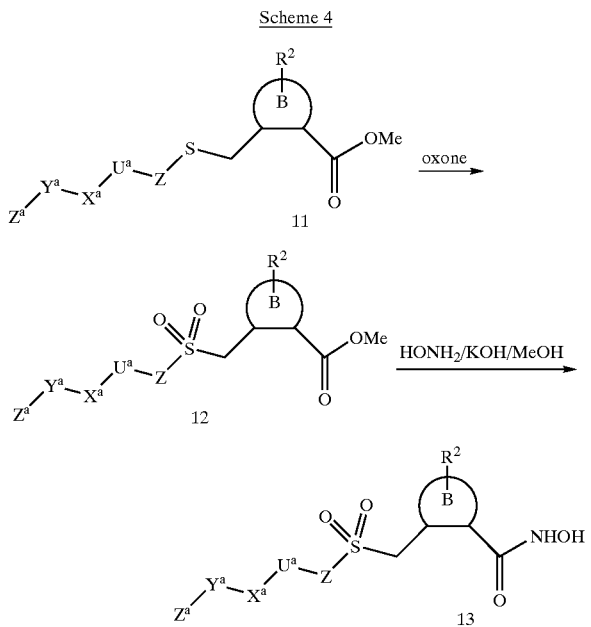

When the B ring is a heterocycle such as a pyrrolidine or piperidine with a protecting group such as Boc on the nitrogen, the protecting group is removed using an acid such as TFA to give a secondary amine 15. Functionalization of the secondary amine by alkylation, reductive amination, acylation, or sulfonylation gives rise to a variety of analogs 16 such as tertiary amines, amides, carbamates, ureas, and sulfonamides. Ester 16 is converted to a hydroxamic acid using the procedures outlined in Scheme 1 and Scheme 4.

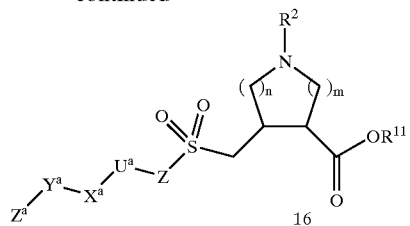

The B ring in formula I can be constructed using the methods depicted in Schemes 6–10. The trans-3,4-disubstituted piperidine derivative 27 can be prepared following the sequence outlined in Scheme 6. Benzylation of N-Cbz-β-amino acid 17 with benzyl bromide in a mixed solvent of DMF/THF using sodium hydride produces the N-benzylated product 18. The carboxylic acid 18 is then coupled with a chiral auxiliary (R)—XH (4-benzyl-2-oxazolidinone) using a coupling agent such as pivaloyl chloride. Alkylation of 19 with tert-butyl bromoacetate using LDA provides the tert-butyl ester 20 that is subjected to a hydrolysis using LiOH/$H_2O_2$. Alkylation of the carboxylic acid 21 with allyl bromide using LDA provides the allylated product 22 with a syn stereochemistry. The carboxylic acid 22 is converted to a benzyl ester 23 and the olefin is converted to an aldehyde 24 by ozonolysis. Hydrogenation using Pd—C as the catalyst gives rise to a piperidine derivative 25 that is subjected to a Boc protection. Borane reduction of 26 affords the alcohol 27.

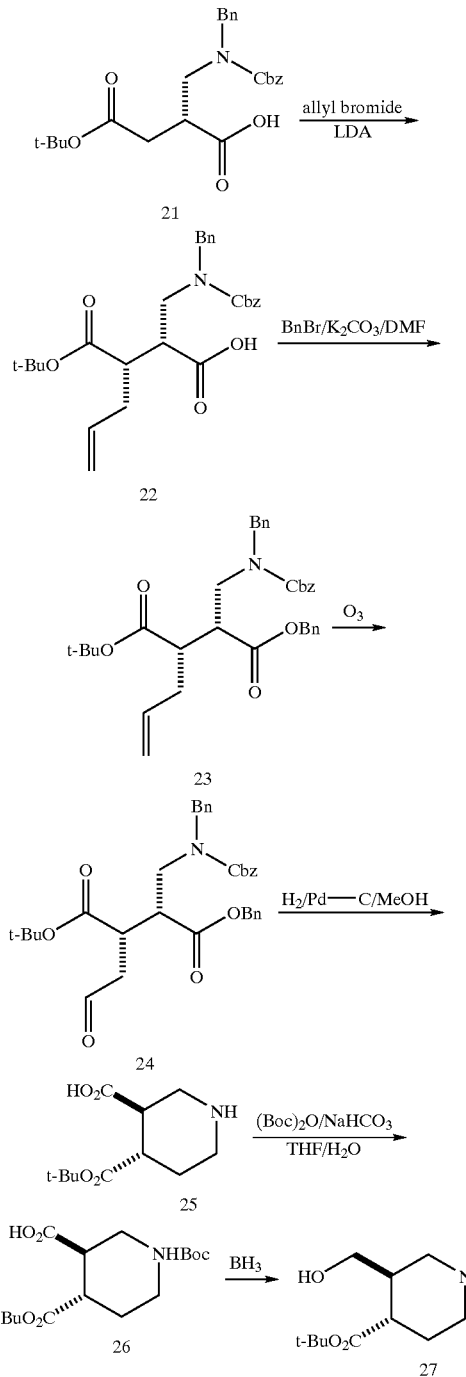

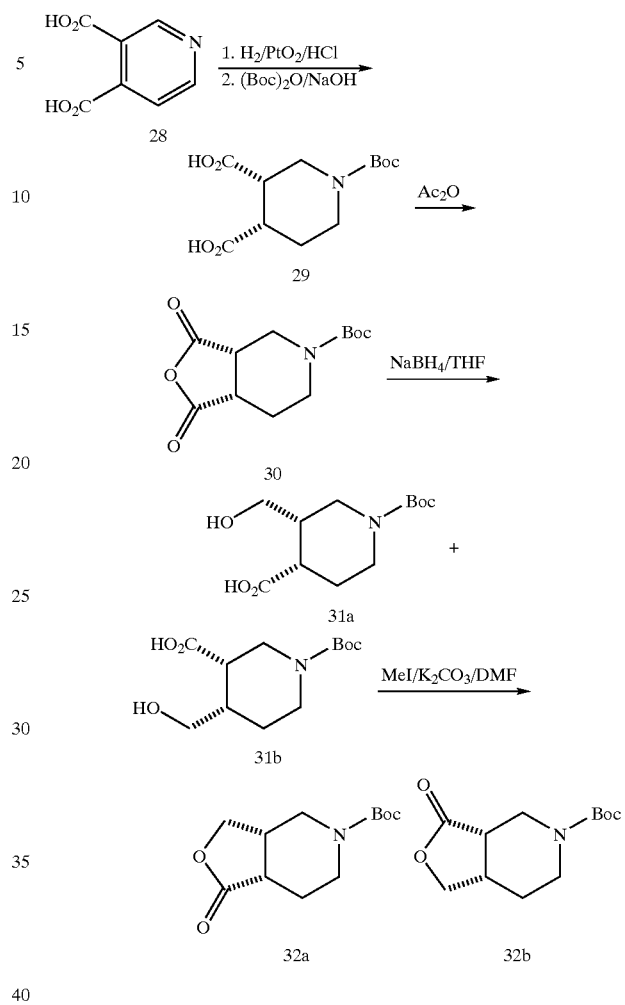

The cis-3,4-disubstituted piperidine derivatives can be prepared starting with 3,4-pyridine dicarboxylic acid 28 (Scheme 7). Hydrogenation using PtO$_2$ as the catalyst in aqueous HCl followed by treatment with (Boc)$_2$O using NaOH as base gives rise to N-Boc-cis-3,4-piperidine dicarboxylic acid 29. The acid is subjected to a treatment with acetic anhydride to give the anhydride 30. Sodium borohydride reduction produces two regioisomers of hydroxycarboxylic acid 31a and 31b. Cyclization by treatment with iodomethane provides two lactones 32a and 32b that are separated using flash chromatography.

The trans-2,3-disubstituted piperidine derivative 40 can be prepared starting with L-aspartic acid β-tert-butyl ester. Alkylation of 40 with benzyl bromide using potassium carbonate in DMF/DMSO provides the tribenzylated intermediate 34. An allyl group was introduced at the β-position by subjecting 34 to a LiHMDS reaction with allyl bromide. After conversion of the olefin in 35 to an alcohol by treatment with 9-BBN, the two diastereomers were separated using flash chromatography. The syn diastereomer is then oxidized using an oxidant such as pyridinium dichromate to give the aldehyde 37. Hydrogenation gives rise to a piperidine derivative 38 that is subjected to a Boc protection. Borane reduction at the carboxylic acid provides the alcohol 40.

Scheme 8

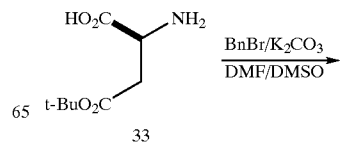

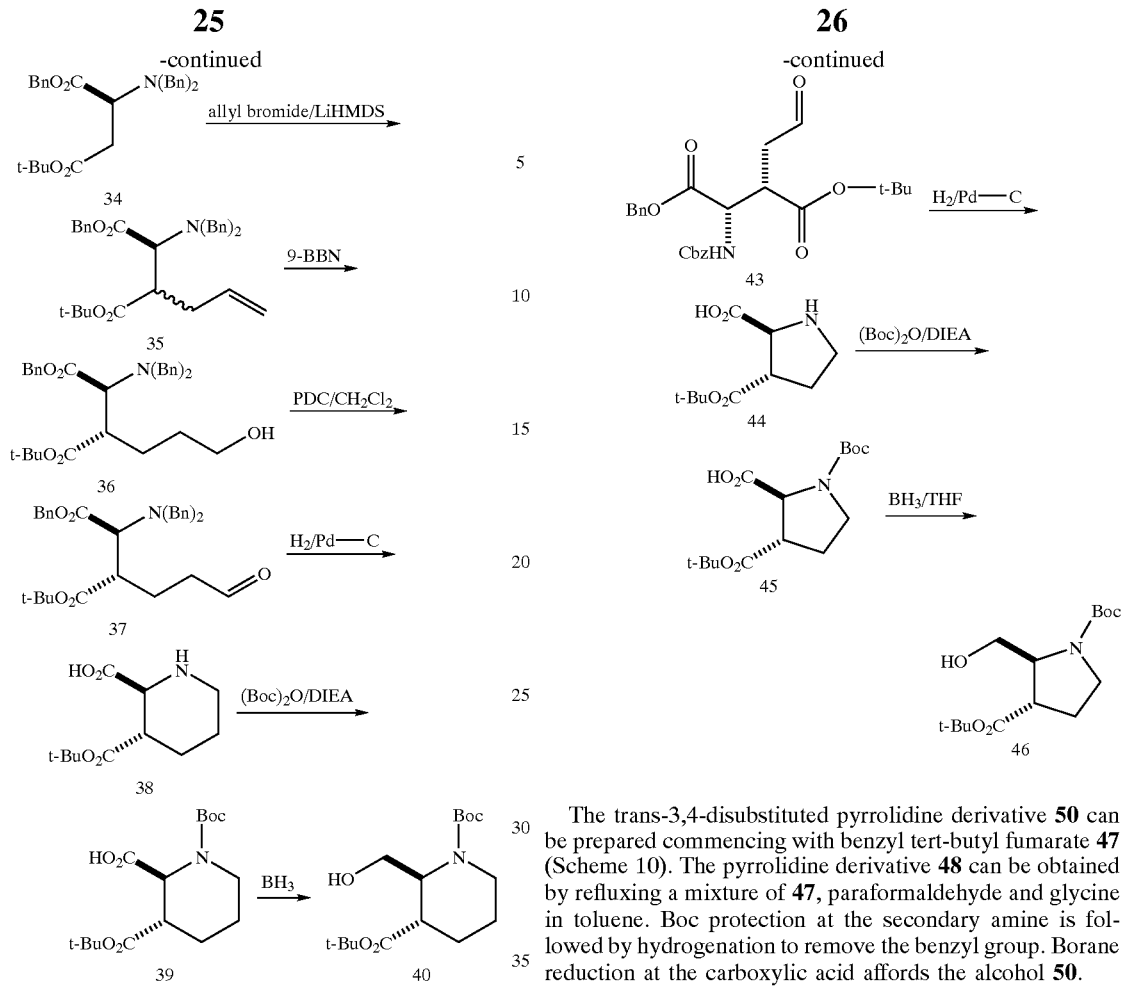

The trans-2,3-disubstituted pyrrolidine derivative 46 can be prepared starting with N-Cbz-L-aspartic acid α-benzyl β-butyl esters 41 (Scheme 9). Alkylation of 41 with allyl bromide using LDA or LHMDS gives rise to the β-allylated product as a mixture of two diastereomers that are seperated using flash chromatography. The syn diastereomer 42 is subjected to ozonolysis to give an aldehyde 43. Hydrogenation provides a pyrrolidine derivative 44. Following Boc protection, the carboxylic acid 45 was subjected to a borane reduction to afford the alcohol 46.

The trans-3,4-disubstituted pyrrolidine derivative 50 can be prepared commencing with benzyl tert-butyl fumarate 47 (Scheme 10). The pyrrolidine derivative 48 can be obtained by refluxing a mixture of 47, paraformaldehyde and glycine in toluene. Boc protection at the secondary amine is followed by hydrogenation to remove the benzyl group. Borane reduction at the carboxylic acid affords the alcohol 50.

The cis-3,4-disubstituted pyrrolidine derivative 57 can be prepared using the sequence outlined in Scheme 11. The N-benzylpyrrolidine derivative 53 can be obtained by refluxing a mixture of N-benzylglycine 51, dimethyl maleate 52, and paraformaldehyde in toluene. Hydrogenation of 53 to remove the benzyl group is carried out in the presence of Boc anhydride that blocks the secondary amine generated. Saponification provides the acid 55 that is subjected to a treatment with acetic anhydride. Sodium borohydride reduction of the anhydride 56 provides the lactone 57.

Scheme 11

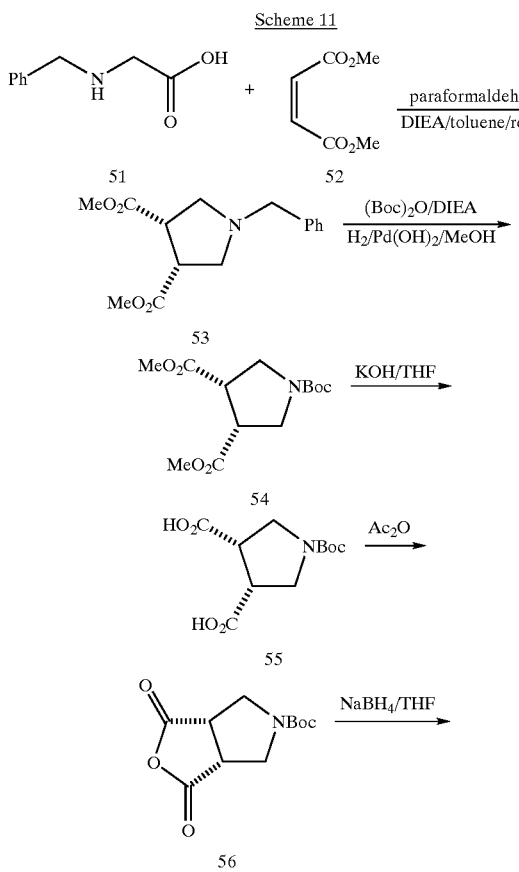

Alternatively, compounds of formula I can be synthesized by introducing an arylthioether at the beginning of the sequence. For example, the intermediate 65 can be prepared starting with N-Cbz-D-aspartic acid β-tert-butyl ester 58. Reduction of 58 using borane provides an alcohol 59. The alcohol is converted to a mesylate 60 that is displaced with 4-mercaptophenol using a base such as sodium hydride to give the sulfide 61. Benzylation at the phenolic OH using potassium carbonate provides 62. Alkylation of 62 with allyl bromide using LDA is followed by Oxone® oxidation. The sulfone 63 is subjected to a 9-BBN reaction to give an alcohol that is oxidized using an oxidant such as pyridinium dichromate. Hydrogenation gives rise to a cis-2,3-disubstituted piperidine derivative the secondary amine of which is then blocked with a Boc group. The intermediate 65 can be converted to a variety of hydroxamic acids using the procedures described previously.

Scheme 12

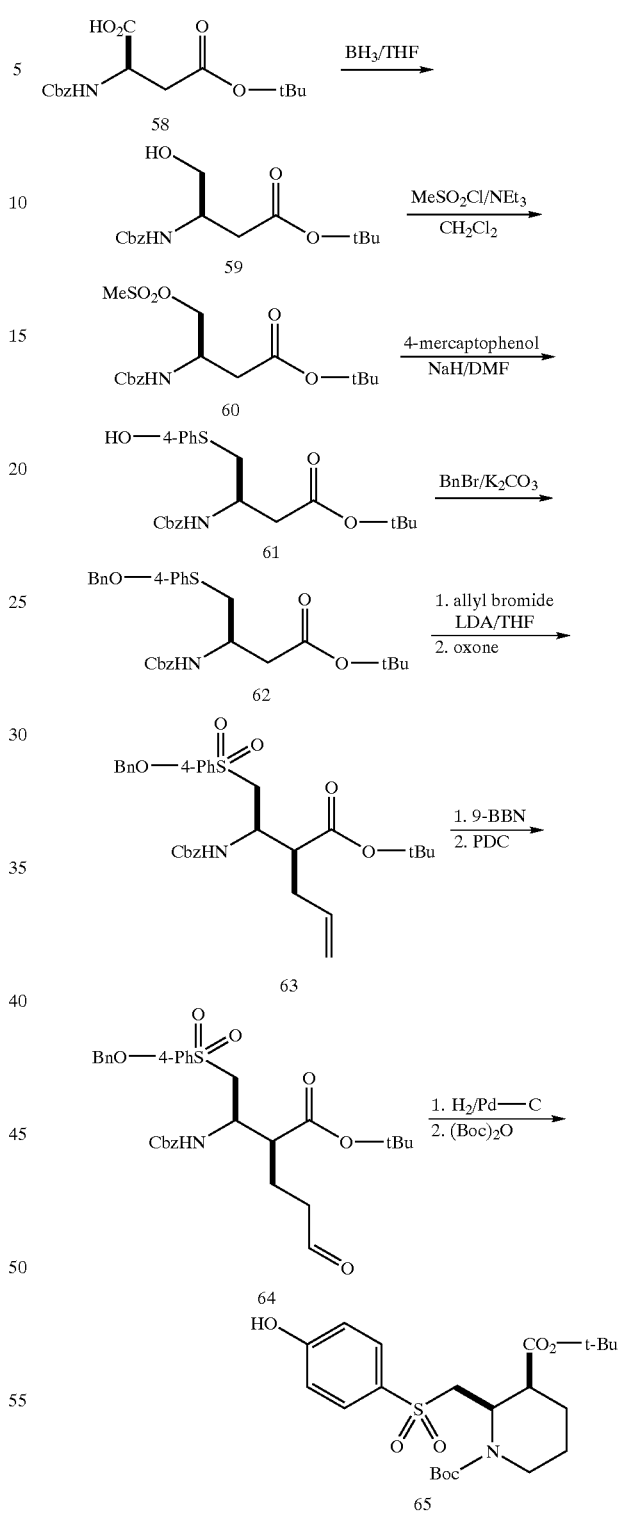

The intermediate 63 can also be subjected to an ozonolysis to give aldehyde 66. Hydrogenation of 66 using a catalyst such as Pd-C gives rise to a cis-2,3-disubstituted pyrrolidine derivative 67. Boc protection at the amino affords the intermediate 68 which can be transformed to a variety of hydroxamic acid following the procedures described previously.

Scheme 13

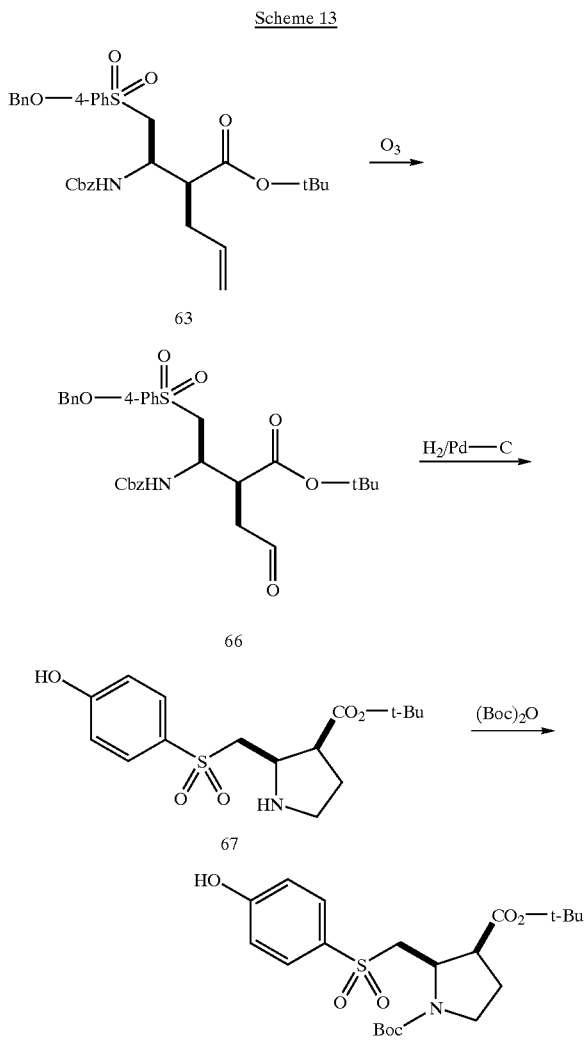

One diastereomer of a compound of Formula I may display superior activity compared with the others. Thus, the following stereochemistries are considered to be a part of the present invention.

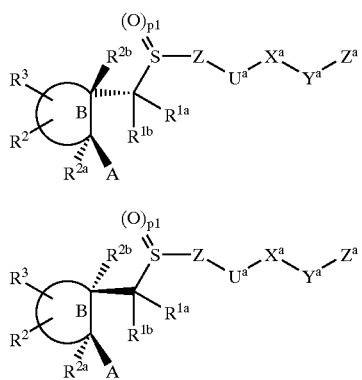

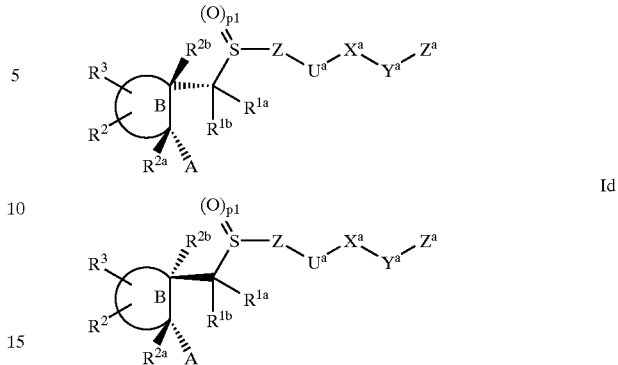

When required, separation of the racemic material can be achieved by HPLC using a chiral column or by a resolution using a resolving agent such as camphonic chloride as in Steven D. Young, et al, *Antimicrobial Agents and Chemotheraphy*, 1995, 2602–2605. A chiral compound of Formula I may also be directly synthesized using a chiral catalyst or a chiral ligand, e.g., Andrew S. Thompson, et al, *Tetr. Lett.* 1995, 36, 8937–8940.

Other features of the invention will become apparent in the course of the following descriptions of exemplary embodiments that are given for illustration of the invention and are not intended to be limiting thereof.

EXAMPLES

Abbreviations used in the Examples are defined as follows: "1×" for once, "2×" for twice, "3×" for thrice, "° C." for degrees Celsius, "eq" for equivalent or equivalents, "g" for gram or grams, "mg" for milligram or milligrams, "mL" for milliliter or milliliters, "$^1$H" for proton, "h" for hour or hours, "M" for molar, "min" for minute or minutes, "MHz" for megahertz, "MS" for mass spectroscopy, "NMR" for nuclear magnetic resonance spectroscopy, "rt" for room temperature, "tlc" for thin layer chromatography, "v/v" for volume to volume ratio. "α" and "β" are stereochemical designations familiar to those skilled in the art.

Example 1

(3R,4S)-N-Hydroxy-1-methyl-3-[({4-[(2-methyl-4-quinolinyl)methoxy]phenyl}sulfonyl)methyl]-4-piperidinecarboxamide bis(trifluoroacetate)

(1a) To a solution of N-benzyloxycarbonyl-β-alanine (25 g, 112 mmol) in THF (400 mL) cooled in an ice bath was slowly added NaH (21.5 g, 448 mmol). After stirring at 0° C. for 30 minutes, a solution of benzylbromide (53.6 mL, 448 mmol) in THF (50 mL) was added. The mixture was stirred at room temperature over the weekend and concentrated under reduced pressure. Water was added and the solution extracted with ether twice. The water layer was acidified with 1 N HCl to pH 3 and extracted with ethyl acetate twice. The extracts were combined and washed with brine, dried (MgSO$_4$), and concentrated. Purification on a silica gel column eluting with 40% ethyl acetate/hexanes followed by crystallization from ethyl acetate/hexanes provided the N-benzyl product (25 g, 71%) as a crystal. MS (M+H)$^+$=314.1.

(1b) To a solution of the carboxylic acid 1a (28.5 g, 91 mmol) and diisopropylethylamine (63.44 mL, 364 mmol) in THF (300 mL) cooled to −30° C. was slowly added pivaloyl chloride (11 mL, 91 mmol). The mixture was stirred at −30° C. for 1 hour. LiCl (3.85 g, 91 mmol) was added followed by (R)-(+)-4-benzyl-2-oxazolidinone (16.12 g, 91 mmol). The mixture was stirred at room temperature overnight and concentrated. Water and ethyl acetate were added and the organic layer was separated, washed with brine, dried (MgSO$_4$), and concentrated. Purification on a silica gel column eluting with 40% ethyl acetate/hexanes followed by crystallization from ethyl acetate/hexanes provided the oxazolidinone derivative (25 g, 57%) as a solid. MS (M+H)$^+$=473.

(1c) To a solution of diisopropylamine (1.95 mL, 13.9 mmol) in THF (7 mL) cooled to −78° C. was added 2.5 M n-butyl lithium (5.8 mL, 14.6 mmol). The solution was stirred at 0° C. for 30 minutes and after cooling back to −78° C., added to a solution of the oxazolidinone derivative 1b (6.0 g, 12.7 mmol) in THF (20 mL) at −78° C. The mixture was stirred at −78° C. for 1 hour and a solution of tert-butyl bromoacetate (2.72 g, 12.7 mmol) in THF (10 mL) was added. Stirring was continued at 0° C. for 3 hours. The solvent was removed under reduced pressure at room temperature and the residue was taken up in ethyl acetate. The EtOAc solution was washed with 10% citric acid and brine, dried (MgSO$_4$), and concentrated. Silica gel chromatography eluting with 25% ethyl acetate/hexanes yielded the desired alkylated product (4.16 g, 56%). MS (M+Na)$^+$=609.5, (1d) To a solution of compound 1c (16.44 g, 28 mmol) in THF (125 mL)/water (72 mL) cooled in an ice bath was added hydrogen peroxide (12.6 mL, 112 mmol). After stirring for 5 minutes, a solution of lithium hydroxide (1.76 g, 42 mmol) in water (20 mL) was added. The mixture was allowed to stir at 0° C. for 90 minutes and sodium sulfite (5 g, 50 mmol) was added. Stirring was continued for 10 min and THF was removed under reduced pressure. The reduced solution was diluted with water (150 mL) and extracted with ether. The water layer was acidified with 10% citric acid and extracted with ethyl acetate 3×. The extracts were combined and washed with brine, dried (MgSO$_4$), and concentrated. Purification on a silica gel column eluting with 3% methanol/methylene chloride provided the desired carboxylic acid (7.78 g, 65%). MS (M−H)$^−$=426.3.

(1e) To a solution of diisopropylamine (4.6 mL, 32.9 mmol) in THF (18 mL) cooled to −78° C. was added 2.5 M n-butyl lithium (12.8 mL, 32.2 mmol). The solution was stirred at 0° C. for 30 minutes and after cooling back to −78° C., added to a solution of the carboxylic acid 1d (5.98 g, 14 mmol) in THF (30 mL) at −78° C. After stirring at −78° C. for 90 minutes, a solution of allyl bromide (1.45 mL, 16.8 mmol) in THF (5 mL) was added. The solution was stirred at 0° C. for 5 hours and poured into a cold 0.5 N HCl solution containing ethyl acetate with vigorous stirring. The organic layer was separated and the water layer was extracted with ethyl acetate twice. The combined organic layers were washed with brine, dried (MgSO$_4$), and concentrated. The crude product was used for the next reaction without purification. MS (M+Na)$^+$=490.3.

(1f) A mixture of the acid 1e (3 g, 6.4 mmol), benzyl bromide (1.17 mL, 9.6 mmol) and potassium carbonate (1.77 g, 12.8 mmol) in DMF (20 mL) was stirred at room temperature overnight. The solvent was removed in vacuo. The residue was taken up in ethyl acetate and the solution was washed with brine, dried (MgSO$_4$), and concentrated. Purification on a silica gel column eluting with 20% ethyl acetate/hexanes provided the desired benzyl ester (1.62 g, 45%). MS (M+Na)$^+$=580.1.

(1g) The ester 1f (4.3 g, 7.72 mmol) was dissolved in methylene chloride (30 mL) and the solution was cooled to −78° C. Into it was bubbled O$_2$ for 10 minutes, followed by O$_3$. The solution turned blue in 10 minutes and bubbling continued for an additional 15 minutes. Nitrogen was bubbled into the mixture until the blue color disappeared. Trimethyl phosphite (1.91 mL, 15.44 mmol) was added and the solution was allowed to stir at room temperature overnight. The reaction was quenched with 1 N HCl. The organic layer was separated, washed with brine, dried (MgSO$_4$), and concentrated. Chromatography on a silica gel column eluting with 20% ethyl acetate/hexanes provided the desired aldehyde (2.4 g, 56%). MS (M+H)$^+$=560.2.

(1h) The aldehyde 1g (2.4 g, 4.29 mmol) in MeOH (100 mL) was hydrogenated at 50 psi overnight using 10% Pd—C (0.72 g) as the catalyst. The catalyst was removed by filtration and the solution was concentrated to give the desired piperidine derivative (1 g, 100%). MS (M+H)$^+$=230.3.

(1i) To a solution of the piperidine derivative 1h (1 g, 4.3 mmol) in THF (5 mL) cooled in an ice bath was added sodium bicarbonate (0.72 g, 8.6 mmol) and Boc anhydride (1.13 g, 5.16 mmol). The mixture was stirred at room temperature for 4 hours, acidified with citric acid solution to pH 3, and extracted with EtOAc twice. The combined extracts were washed with brine, dried (MgSO$_4$), and concentrated. Chromatography on a silica gel column eluting with 5% MeOH/CH$_2$Cl$_2$ provided the Boc protected product (0.8 g, 56%). MS (M+H)$^+$=330.2.

(1j) To a solution of 1i (0.6 g, 1.8 mmol) in THF (5 mL) cooled in an ice bath was added a solution of 1 M borane in THF (3.6 mL). The solution was stirred for 3 hours and quenched with sodium bicarbonate solution. EtOAc was added. The organic phase was separated, washed with brine, dried (MgSO$_4$) and concentrated. Purification on a silica gel column eluting with EtOAc/hexanes (2:1) provided the desired alcohol (0.48 g, 84%). MS (M+H)$^+$=316.2.

(1k) To a solution of 1j (0.48 g, 1.52 mmol) in CH$_2$Cl$_2$ (5 mL) cooled in an ice bath was added triethylamine (0.42 mL, 3 mmol) followed by methanesulfonyl chloride (261 mg, 2.28 mmol). The mixture was stirred at room temperature overnight and concentrated. The residue was taken up in EtOAc and washed with sodium bicarbonate and brine, dried (MgSO$_4$), and concentrated. Flash chromatography eluting with EtOAc/hexanes (2:1) provided the desired mesylate (0.54 g, 90%). MS (M+Na)$^+$=416.3.

(1l) To a solution of 4-mercaptophenol (0.353 g, 2.8 mmol) in DMF (5 mL) cooled in an ice bath was added NaH (0.224 g, 5.6 mmol). After stirring for 10 min, compound 1k (0.54 g, 1.38 mmol) was added. The mixture was stirred at room temperature overnight. EtOAc was added and the solution was washed with citric acid 2×, brine 2×, dried (MgSO$_4$) and concentrated. Chromatography on a silica gel column eluting with 50% EtOAc/hexanes provided the desired product (0.42 g, 72%). MS (M+H)$^+$=424.1.

(1m) A mixture of 1l (423 mg, 1 mmol), 4-chloromethyl-2-methylquinoline hydrochloride (228 mg, 1 mmol) and potassium carbonate (276 mg, 1 mmol) in DMF (5 mL) was stirred at 80° C. for 2 hours. After cooling down, EtOAc was added. The solution was washed with brine 3×, dried (MgSO$_4$) and concentrated. Chromatography on a silica gel column eluting with EtOAc/hexanes (2:1) provided the desired product (510 mg, 88%). MS (M+H)$^+$=579.1.

(1n) To a solution of 1m (510 mg, 0.88 mmol) in MeOH (2 mL) and THF (2 mL) was added a solution of Oxone® (614 mg, 1 mmol) in water (2 mL). After stirring at room temperature for 4 hours, EtOAc was added. The solution was washed with brine 3×, dried (MgSO$_4$), and concentrated.

Chromatography on a silica gel column eluting with EtOAc/hexanes (2:1) provided the desired sulfone derivative (310 mg, 58%). MS (M+H)$^+$=611.2.

(1o) Compound in was dissolved in a mixed solvent of CH$_2$Cl$_2$ (2 mL) and TFA (2 mL). After stirring for 3 hours at room temperature, the solution was concentrated to give the desired product. MS (M+H)$^+$=455.1.

(1p) To a solution of 1o (100 mg, 0.146 mmol), 37% formaldehyde solution (0.041 mL, 0.5 mmol) and DIEA (0.105 mL, 0.6 mmol) in DMF (3 mL) was added sodium triacetoxyborohydride (47 mg, 0.22 mmol). The mixture was stirred for 2 hours at room temperature. Purification by reversed phase HPLC provided the N-methylated product (74 mg, 72%) as a powder. MS (M+H)$^+$=469.1.

(1q) Compound 1p (74 mg, 0.106 mmol) was dissolved in DMF (3 mL). The solution was cooled to −30° C. Propyl chloroformate (0.024 mL, 0.21 mmol) and N-methylmorpholine were added. After stirring for 30 min, a solution of hydroxylamine hydrochloride (30 mg, 0.32 mmol) and N-methylmorpholine (0.058 mL, 0.53 mmol) in DMF (1 mL) was added. Stirring was continued for 1 h at −30° C. Purification by reversed phase HPLC provided the hydroxamic acid (38 mg, 50%) as a powder. MS (M+H)$^+$=484.1.

Example 2

(3R,4S)-N-Hydroxy-1-isopropyl-3-[({4-[(2-methyl-4-quinolinyl)methoxy]phenyl}sulfonyl)methyl]-4-piperidinecarboxamide bis(trifluoroacetate)

This compound was prepared using procedures analogous to those described for Example 1. MS (M+H)$^+$=512.1.

Example 3 tert-Butyl (3S,4S)-4-[(hydroxyamino)carbonyl]-3-[({4-[(2-methyl-4-quinolinyl)methoxy]phenyl}sulfonyl)methyl]-1-piperidinecarboxylate trifluoroacetate (3a) 3,4-Pyridinedicarboxylic acid (25 g, 150 mmol) was dissolved in aqueous 1 N HCl solution (400 mL) in a Parr bottle. PtO2 (5 g) was added. The mixture was hydrogenated at 55 psi overnight. The catalyst was filtered off and the filtrate concentrated. The residue was taken up in water (250 mL) and cooled down in an ice bath. To it was added NaOH (18 g, 450 mmol) followed by Boc anhydride (32.7 g, 150 mmol). The mixture was stirred overnight and extracted with ether. The water layer was acidified with 1 N HCl to pH 3, extracted with EtOAc 2×. The combined extracts were washed with brine 2×, dried (MgSO$_4$), and concentrated. Crystallization from EtOAc provided cis-N-Boc-3,4-piperidinedicarboxylic acid (31 g, 75%) as a crystal. MS (M+H)$^+$=274.2.

(3b) Compound 3a (5.46 g, 20 mmol) was dissolved in THF (20 mL) and acetic anhydride (20 mL) was added. The solution was stirred at room temperature for 3 h and concentrated to give a solid. The solid was dissolved in THF (100 mL) and the solution was cooled in an ice bath. To it was slowly added sodium borohydride (0.75 g, 20 mmol) over a period of 30 min. Stirring was continued for 3 h at 0–10° C. The reaction was quenched with citric acid solution. EtOAc was added. The organic phase was separated, washed with citric acid 2×, brine 2×, dried (MgSO$_4$), and concentrated to provide a mixture of cis-N-Boc-3-hydroxymethyl-4-piperidinecarboxylic acid and cis-N-Boc-4-hydroxymethyl-3-piperidinecarboxylic acid. The mixture was not separated and was directly used for the next reaction. MS (M+H)$^+$=260.3.

(3c) To a solution of 3b (4.5 g, 17.3 mmol) in DMF (30 mL) was added iodomethane (1.84 mL, 30 mmol) followed by potassium carbonate (4.1 g, 30 mmol). The mixture was stirred at room temperature for 2 h and diluted with EtOAc (200 mL). The solution was washed with brine 4×, dried (MgSO$_4$) and concentrated. Chromatography on a silica gel column eluting with 50% EtOAc/hexanes provided the fast moving lactone (1.8 g, 43%) as a solid and the slow moving lactone (1.9 g, 44%) as an oil. MS for both regioisomers: (M+Na+CH$_3$CN)$^+$=305.1.

(3d) To a solution of 4-mercaptophenol (1.9 g, 15 mmol) in DMF (20 mL) cooled in an ice bath was added NaH (0.52 g, 13 mmol). After stirring for 5 min under nitrogen, a solution of the fast moving isomer from (3c) (1.8 g, 7.5 mmol) in DMF (10 mL) was added. The mixture was stirred at 80° C. for 3 h. After cooling to room temperature, EtOAc was added. The solution was washed with citric acid solution 2×, brine 2×, dried (MgSO$_4$), and concentrated. Crystallization from EtOAc/hexanes provided the sulfide product (2.1 g, 76%) as a crystal. MS (M+H)$^+$=368.2.

(3e) To a solution of 3d (2.1 g, 6 mmol) in DMF (10 mL) was added iodomethane (1.3 g, 9 mmol) followed by potassium carbonate (1.1 g, 8 mmol). The mixture was stirred at room temperature for 2 h. EtOAc was added. The solution was washed with citric acid 2×, brine 2×, dried (MgSO$_4$), and concentrated. Chromatography on a silica gel column eluting with EtOAc/hexanes (2:1) provided the methyl ester (1.8 g, 79%) as an oil. MS (M+H)$^+$=382.2.

(3f) A mixture of 3e (1.8 g, 4.7 =mol), 4-chloromethyl-2-methylquinoline hydrochloride (1.14 g, 5 mmol) and potassium carbonate (1.38 g, 10 mmol) in DMF (10 mL) was stirred at 50° C. overnight. EtOAc was added. The solution was washed with brine 4×, dried (MgSO$_4$), and concentrated. Purification on a silica gel column eluting with 50% EtOAc/hexanes provided the quinoline derivative (1.9 g, 76%) as a solid. MS (M+H)$^+$=537.2.

(3g) To a solution of 3f (1.8 g, 3.35 mmol) in MeOH (20 mL) and THF (10 mL) was added a solution of Oxone® (3.1 g, 5 mmol) in water (20 mL). The mixture was stirred at room temperature for 2 hours. EtOAc was added. The solution was washed with sodium bicarbonate 2× and brine 2×, dried (MgSO$_4$), and concentrated to give the sulfone derivative (1.9 g, 100%) as a solid. MS (M−H)$^−$=567.2.

(3h) Hydroxylamine hydrochloride (2.34 g, 33.7 mmol) was dissolved in hot MeOH (12 mL). To it was added a solution of KOH (2.81 g, 50.1 mmol) in MeOH (7 mL). After cooling to room temperature, the salt formed was filtered off to provide a 1.7 M solution of hydroxylamine in MeOH. Compound 3g (300 mg, 0.53 mmol) was dissolved in the 1.7 M hydroxylamine solution (3 mL). The solution was stirred at room temperature for 20 min. Acetic acid (0.5 mL) was added and the solution was concentrated. The residue was dissolved in DMSO and purified by reversed phase HPLC to give the hydroxamic acid (190 mg, 63%) as a powder. MS (M+H)$^+$=570.2.

Example 4

(3S,4S)-N-Hydroxy-3-[({4-[(2-methyl-4-quinolinyl)methoxy]phenyl}sulfonyl)methyl]-4-piperidinecarboxamide bis(trifluoroacetate)

Compound 3h (100 mg) was dissolved in a solution of 50% TFA in CH$_2$Cl$_2$ (10 mL). After stirring at room temperature for 30 min. the solution was concentrated. The residue was taken up in water/acetonitrile. Lyophilization provided the NH product as a powder. MS (M+H)$^+$=470.1.

Example 5

(3S,4S)-N-Hydroxy-1-methyl-3-[({4-[(2-methyl-4-quinolinyl)methoxy]phenyl}sulfonyl)methyl]-4-piperidinecarboxamide bis(trifluoroacetate)

(5a) Compound 3g (500 mg, 0.88 mmol) was dissolved in 4 N HCl in dioxane (20 mL). After stirring at room temperature for 2 hours, the solution was concentrated to give the NH product (476 mg, 100%) as a solid. MS (M+H)$^+$=469.2.

(5b) To a solution of 5a (150 mg, 0.277 mmol) in DMF (2 mL) was added 37% formaldehyde solution (81 mg, 1 mmol) followed by sodium triacetoxyborohydride (106 mg, 0.5 mmol) and triethylamine (100 mg, 1 mmol). The mixture was stirred at room temperature for 3 hours. Purification by reversed phase HPLC provided the N-methyl derivative (150 mg, 77%) as a powder. MS (M+H)$^+$=483.1.

(5c) Compound 5b was treated with 1.7 M hydroxylamine solution following the procedure described in (3 h) to provide the hydroxamic acid as a powder. MS (M+H)$^+$=484.1.

Example 6

(3S, 4S)-N-Hydroxy-1-isopropyl-3-[({4-[(2-methyl-4-quinolinyl)methoxy]phenyl}sulfonyl)methyl]-4-piperidinecarboxamide bis(trifluoroacetate)

This compound was prepared using procedures analogous to those described for Example 5. MS (M+H)$^+$=512.1.

Example 7

(3S,4S)-N-Hydroxy-3-[({4-[(2-methyl-4-quinolinyl)methoxy]phenyl}sulfonyl)methyl]-1-propyl-4-piperidinecarboxamide bis(trifluoroacetate)

This compound was prepared using procedures analogous to those described for Example 5. MS (M+H)$^+$=512.1.

Example 8

(3S,4S)-1-Butyl-N-hydroxy-3-[({4-[(2-methyl-4-quinolinyl)methoxy]phenyl}sulfonyl)methyl]-4-piperidinecarboxamide bis(trifluoroacetate)

This compound was prepared using procedures analogous to those described for Example 5. MS (M+H)$^+$=526.2.

Example 9

(3S, 4S)-N-Hydroxy-1-isobutyl-3-[({4-[(2-methyl-4-quinolinyl)methoxy]phenyl}sulfonyl)methyl]-4-piperidinecarboxamide bis(trifluoroacetate)

This compound was prepared using procedures analogous to those described for Example 5. MS (M+H)$^+$=526.2.

Example 10

(3S,4S)-N-Hydroxy-3-[({4-[(2-methyl-4-quinolinyl)methoxy]phenyl}sulfonyl)methyl]-1-(2-propynyl)-4-piperidinecarboxamide bis(trifluoroacetate)

(10a) To a solution of 5a (200 mg, 0.37 mmol) in DMF (2 mL) was added propargyl bromide (89 mg, 80% solution in toluene, 0.6 mmol) followed by potassium carbonate (207 mg, 1.5 mmol). The mixture was stirred at room temperature for 2 hours. Purification by reversed phase HPLC provided the propargyl derivative (150 mg, 55%) as a powder. MS (M+H)$^+$=507.1.

(10b) Compound 10a was treated with 1.7 M hydroxylamine solution following the procedure described in (3 h) to provide the hydroxamic acid as a powder. MS (M+H)$^+$=508.1.

Example 11

(3S,4S)-1-Allyl-N-hydroxy-3-[({4-[(2-methyl-4-quinolinyl)methoxy]phenyl}sulfonyl)methyl]-4-piperidinecarboxamide bis(trifluoroacetate)

This compound was prepared using procedures analogous to those described for Example 10. MS (M+H)$^+$=510.1.

Example 12 tert-Butyl (3R,4R)-3-[(hydroxyamino)carbonyl]-4-[({4-[(2-methyl-4-quinolinyl)methoxy]phenyl}sulfonyl)methyl]-1-piperidinecarboxylate trifluoroacetate (12a) The slow moving isomer from (3c) was treated with 4-mercaptophenol following the procedure described in (3d) to provide the desired sulfide product. MS (M+H)$^+$=368.2.

(12b) Compound 12a was treated with iodomethane following the procedure described in (3e) to provide the desired methyl ester. MS (M+H)$^+$=382.2.

(12c) Compound 12b was treated with 4-chloromethyl-2-methylquinoline following the procedure described in (3f) to provide the quinoline derivative. MS (M+H)$^+$=537.2.

(12d). Oxidation of 12c using Oxone® following the procedure described in (3g) provided the desired sulfone derivative. MS (M+H)$^+$=569.2.

(12e) Compound 12d was converted to a hydroxamic acid following the procedure described in (3 h). MS (M+H)$^+$=570.2.

Example 13

(3R,4R)-N-Hydroxy-4-[({4-[(2-methyl-4-quinolinyl)methoxy]phenyl}sulfonyl)methyl]-3-piperidinecarboxamide bis(trifluoroacetate)

Following the procedure described for Example 4, compound 12e was treated with 50% TFA/CH$_2$Cl$_2$ to afford the NH analog. MS (M+H)$^+$=470.1.

Example 14

(3R,4R)-N-Hydroxy-1-methyl-4-[({4-[(2-methyl-4-quinolinyl)methoxy]phenyl}sulfonyl)methyl]-3-piperidinecarboxamide bis(trifluoroacetate)

This compound was prepared by removal of the Boc group in 12d followed by reductive amination with formaldehyde and conversion of the methyl ester to a hydroxamic acid using procedures analogous to those described for Example 5. MS (M+H)$^+$=484.1.

Example 15

(3R,4R)-N-Hydroxy-1-isopropyl-4-[({4-[(2-methyl-4-quinolinyl)methoxy]phenyl}sulfonyl)methyl]-3-piperidinecarboxamide bis(trifluoroacetate)

This compound was prepared by removal of the Boc group in 12d followed by reductive amination with acetone and conversion of the methyl ester to a hydroxamic acid using procedures analogous to those described for Example 5. MS (M+H)$^+$=512.1.

Example 16

(2S,3S)-N-Hydroxy-2-[({4-[(2-methyl-4-quinolinyl) methoxy]phenyl}sulfonyl)methyl]-3-piperidinecarboxamide bis(trifluoroacetate)

(16a) To a suspension of L-aspartic acid tert-butyl ester (25 g, 132 mmol) in DMF (250 mL) and DMSO (50 mL) was added benzyl bromide (79 mL, 462 mmol) followed by potassium carbonate (55 g, 396 mmol). The mixture was mechanically stirred at 50° C. overnight, cooled to room temperature and diluted with water (500 mL). The solution was extracted with ethyl acetate three times. The combined extracts were washed with brine 3x, dried (MgSO$_4$) and concentrated. Purification on a silica gel column eluting with ethyl acetate (10%)/hexane provided the tri-benzylated product (60 g, 99%) as a viscous oil. MS (M+H)$^+$=460.

(16b) To a solution of the tri-benzylated compound 16a (30 g, 65.35 mmol) in THF (500 mL) cooled at −78° C. was added a 1 M solution of lithium bis(trimethylsilyl)amide in THF (72 mL). The mixture was stirred at −78° C. for 1 hour and allyl bromide (6.78 mL, 78.4 mmol) was added. The temperature was raised to −10° C. and stirring was continued at −10° C. for 3 hours. The reaction was quenched with 10% citric acid solution followed by dilution with brine. The mixture was extracted with ethyl acetate three times. The combined extracts were washed with brine, dried (MgSO$_4$), and concentrated. Chromatography on a silica gel column eluting with ethyl acetate (20%)/hexanes produced the allylated product (22 g, 67%) as a viscous oil. MS (M+H)$^+$=500.1.

(16c) To a solution of the allylated product 16b (21 g, 42 mmol) in THF (50 mL) cooled in an ice bath was added a 0.5 M solution of 9-BBN (168 mL, 84 mmol). The mixture was stirred at room temperature overnight and cooled in an ice bath. To it was added a solution of sodium acetate (69 g) in water (100 mL) followed by a solution of 33% H$_2$O$_2$ (68.5 mL). The mixture was stirred at room temperature for 3 hours and extracted with ethyl acetate three times. The combined extracts were washed with brine 3x, dried (MgSO$_4$), and concentrated. The crude product was a mixture of two isomers (syn and anti, 1:1 ratio) which were separated by chromatography on a silica gel column eluting with ethyl acetate (30%)/hexanes. The fast moving isomer was characterized as the desired syn isomer (9.7 g, 44%). MS (M+H)$^+$=518.1.

(16d) To a solution of the alcohol 16c (9.3 g, 18 mmol) in methylene chloride (100 mL) cooled in an ice bath was added Dess-Martin reagent (10.6 g, 25 mmol). The mixture was stirred at room temperature for 5 hours and filtered through a pad of silica gel. The silica gel was thoroughly rinsed with CH$_2$Cl$_2$. The filtrate was concentrated. The residue was taken up in ethyl acetate and the solution was washed with brine 3x, dried (MgSO$_4$), and concentrated. Purification on a silica gel column eluting with ethyl acetate (40%)/hexanes produced the aldehyde (5.6 g, 60%) as a viscous oil. MS (M+H)$^+$=516.3.

(16e) A solution of the aldehyde 16d (5.15 g, 10 mmol) in methanol (100 mL) in a Parr bottle was hydrogenated under a pressure of 50 psi for 5 hours using 10% palladium on carbon (1.0 g) as the catalyst. The catalyst was filtered off and the solution was concentrated to give the crude cyclized product (2.3 g) that was used for the next reaction without purification. MS (M+H)$^+$=230.1.

(16f) To a solution of 16e (260 mg, 1.13 mmol) in water (2 mL) was added sodium bicarbonate (250 mg, 3 mmol) followed by a solution of Boc anhydride (327 mg, 1.5 mmol). The mixture was stirred at room temperature for 4 hours. EtOAc was added. The solution was washed with 10% citric acid 2x, brine 2x, dried (MgSO$_4$) and concentrated. Purification on a silica gel column eluting with 5% MeOH/CH$_2$Cl$_2$ provided the Boc protected product (260 mg, 70%) as a solid. MS (M+H)$^+$=330.2.

(16g) To a solution of 16f (250 mg, 0.76 mmol) in THF (1 mL) cooled in an ice bath was added 1 M BH$_3$ in THF (2 mL). The solution was stirred at room temperature for 5 hours under nitrogen. EtOAc was added followed by sodium bicarbonate solution. The EtQAc layer was separated, washed with brine 3x, dried (MgSO$_4$) and concentrated. Chromatography on a silica gel column eluting with 50% EtOAc/hexanes provided the alcohol (160 mg, 67%) as an oil. MS (M+H)$^+$=316.2.

(16h) To a solution of 16g (150 mg, 0.476 mmol) in CH$_2$Cl$_2$ (2 mL) cooled in an ice bath was added DIEA (258 mg, 2 mmol) followed by methanesulfonyl chloride (92 mg, 0.8 mmol). After stirring for 3 hours, the solution was concentrated. The residue was taken up in EtOAc. The solution was washed with brine 3x, dried (MgSO$_4$) and concentrated to provide the mesylate (190 mg, 100%) that is pure enough for the next reaction. MS (M+H)$^+$=394.

(16i) To a solution of 4-mercaptophenol (126 mg, 1 mmol) in DMF (1 mL) cooled in an ice bath was added NaH (80 mg, 60% dispersion in mineral oil, 2 mmol). After stirring for 5 min under nitrogen, a solution of compound 16h (187 mg, 0.476 mmol) in DMF (1 mL) was added. The mixture was stirred at room temperature overnight. EtOAc was added. The solution was washed with citric acid 2x, brine 2x, dried (MgSO$_4$) and concentrated. Chromatography on a silica gel column eluting with EtOAc/hexanes (1:2) provided the sulfide product (120 mg, 57%). MS (M+H)$^+$=424.1.

(16j) A mixture of compound 16i (120 mg, 0.2837 mmol), 4-chloromethyl-2-methylquinoline hydrochloride (114 mg, 0.5 mmol) and potassium carbonate (276 mg, 2 mmol) in DMF (2 mL) was stirred at 50° C. overnight. EtOAc was added. The solution was washed with brine 3x, dried (MgSO$_4$) and concentrated. Chromatography on a silica gel column eluting with 50% EtOAc/hexanes provided the desired product (160 mg, 97%). MS (M+H)$^+$=579.3.

(16k) To a solution of compound 16j (150 mg, 0.259 mmol) in MeOH (2 mL) and THF (1 mL) was added a solution of Oxone® (368 mg, 0.6 mmol) in water (3 mL). The mixture was stirred at room temperature for 2 hours. EtOAc was added. The solution was washed with brine 3x, dried (MgSO$_4$) and concentrated. The residue was taken up in DMSO (2 mL) and purified by reversed phase HPLC to give the sulfone derivative as a powder. MS (M+H)$^+$=611.3.

(16l) Compound 16k (150 mg) was dissolved in a mixed solvent of TFA (2 mL) and CH$_2$Cl$_2$ (2 mL). After stirring at room temperature for 4 hours, the solution was concentrated to give the desired product as a bis-TFA salt. MS (M+H)$^+$=455.1.

(16m) To a solution of compound 16l (68 mg, 0.1 mmol) in DMF (2 mL) cooled in an ice bath was added PyBOP (78 mg, 0.15 mmol) followed by a solution of hydroxylamine hydrochloride (21 mg, 0.3 mmol) and NMM (71 mg, 0.7 mmol) in DMF (1 mL). The mixture was stirred for 1 h. Purification by reversed phase HPLC provided the hydroxamic acid (50 mg, 71%) as a powder. MS (M+H)$^+$=470.2.

Example 17

(2S,3S)-N-Hydroxy-1-methyl-2-[({4-[(2-methyl-4-quinolinyl)methoxy]phenyl}sulfonyl)methyl]-3-piperidinecarboxamide bis(trifluoroacetate)

(17a) To a solution of compound 16l (140 mg, 0.205 mmol) in DMF (2 mL) were added formaldehyde (81 mg, 37% solution in water, 1 mmol), sodium triacetoxyborohydride (84 mg, 0.4 mmol) and triethylamine (100 mg, 1 mmol). The mixture was stirred at room temperature for 2 hours. Purification by reversed phase HPLC provided the N-methyl analog (100 mg, 71%) as a powder. MS (M+H)$^+$= 469.2.

(17b) Compound 17a was converted to a hydroxamic acid following the procedure described in (16 m). MS (M+H)$^+$= 484.2.

Example 18

(2R,3S)-N-Hydroxy-2-[({4-[(2-methyl-4-quinolinyl)methoxy]phenyl}sulfonyl)methyl]-3-piperidinecarboxamide bis(trifluoroacetate)

(18a) To a solution of N-Cbz-D-aspartic acid β-tert-butyl ester hydrate (8.25 g, 25.5 mmol) in THF (20 mL) was added a solution of BH$_3$ in THF (200 mL) in batches over a period of 2 hours at room temperature. After stirring for another hour, a solution of saturated NaHCO$_3$ (200 mL) was then added slowly. The solution was diluted with EtOAc. The organic phase was separated, washed with brine 3×, dried (MgSO$_4$), and concentrated. Flash chromatography eluting with 50% EtOAc/hexanes provided the alcohol (4.4 g, 56%) as an oil. MS (M+H)$^+$=310.1.

(18b) To a solution of compound 18a (4.4 g, 14.23 mmol) in CH$_2$Cl$_2$ cooled in an ice bath was added triethylamine (2.04 mL, 20.2 mmol) followed by methanesulfonyl chloride (1.87 mL, 16.32 mmol). After stirring for 1.5 h, the solution was concentrated. The residue was taken up in EtOAc. The solution was washed with brine 3×, dried (MgSO$_4$) and concentrated. Chromatography on a silica gel column eluting with 40% EtOAc/hexanes provided the desired mesylate (5.2 g, 94%). MS (M+H)$^+$=388.

(18c) To a solution of 4-mercaptophenol (5.97 g, 42.28 mmol) in DMF (60 mL) cooled in an ice bath was slowly added NaH (3.63 g, 60% dispersion in mineral oil, 75.65 mmol). After stirring for 5 min under nitrogen, a solution of compound 18b (6.1 g, 15.76 mmol) in DMF (10 mL) was added. The mixture was stirred at room temperature overnight. EtOAc was added. The solution was washed with citric acid 2×, brine 3×, dried (MgSO$_4$) and concentrated. Flash column eluting with 30% EtOAc/hexanes provided the sulfide product (5 g, 76%). MS (M+H)$^+$=418.1.

(18d) A mixture of compound 18c (6 g, 14.38 mmol), potassium carbonate (5.96 g, 43.14 mmol), and benzyl bromide (3.42 mL, 28.76 mmol) in DMF (20 mL) was stirred at 50° C. for 2 hours. After cooling to room temperature, EtOAc was added. The solution was washed with brine 3×, dried (MgSO$_4$) and concentrated. Flash chromatography eluting with 30% EtOAc/hexanes provided the desired product (5.6 g, 77%). MS (M+H)$^+$=508.1.

(18e) To a solution of diisopropylamine (3.24 mL, 23.19 mmol) in THF (20 mL) cooled to −78° C. was added 2.5 M n-BuLi (9.27 mL, 23.18 mmol). The solution was stirred at 0° C. for 30 min and cooled back to −78° C. To it was added a solution of compound 18d (5.6 g, 11.04 mmol) in THF (30 mL) at −78° C. After stirring at −78° C. for 1 h, allyl bromide (1.05 mL, 12.14 mmol) was added. The mixture was stirred at −30° C. for 4 hours and the reaction was quenched with 10% citric acid solution (10 mL). EtOAc was added. The solution was washed with citric acid 1×, brine 3×, dried (MgSO$_4$) and concentrated. Chromatography on a silica gel column eluting with 20% EtOAc/hexanes provided the desired product (4.5 g, 75%). MS (M+H)$^+$=548.2.

(18f) To a solution of compound 18e (4.5 g, 8.22 mmol) in THF (30 mL) and MeOH (20 mL) was added a solution of Oxone® (11.11 g, 18.08 mmol). The mixture was stirred at room temperature for 2 h. EtOAc was added and insoluble materials were filtered off. The filtrate was washed with brine 3×, dried (MgSO$_4$) and concentrated. Column chromatography eluting with 20% EtOAc/hexanes provided the desired product (3.3 g, 70%). MS (M+H)$^+$=580.1.

(18g) To a solution of compound 18f (4.4 g, 7.6 mmol) in THF (10 mL) cooled in an ice bath was added a solution of 0.5 M 9-BBN in THF (30 mL). The solution was stirred at room temperature for 6 hours. Sodium acetate (2 g) in water (10 mL) and H$_2$O$_2$ (4 mL) were added. After stirring for another 30 min, EtOAc was added. The solution was washed with brine 3×, dried (MgSO$_4$) and concentrated. Column chromatography eluting with 60% EtOAc/hexanes provided the desired alcohol (3.05 g, 67%). MS (M+H)$^+$=598.1.

(18h) A mixture of compound 18g (3.05 g, 5.1 mmol) and pyridinium dichromate (3.05 g, 8.1 mmol) in CH$_2$Cl$_2$ (200 mL) was stirred at room temperature for 2 days and filtered through a thin pad of silica gel. The silica gel was washed thoroughly with CH$_2$Cl$_2$ for several times. The filtrate was concentrated. Purification on a silica gel column eluting with 50% EtOAc/hexanes provided the desired aldehyde (2.17 g, 71%). MS (M+H)$^+$=596.1.

(18i) A mixture of compound 18h (2.17 g, 3.64 mmol) and 10% Pd—C (0.5 g) in MeOH (200 mL) was hydrogenated at 50 psi for 2 hours. The catalyst was filtered off and the filtrate was concentrated to give the crude cyclized product (1.23 g, 95%). MS (M+H)$^+$=356.2.

(18j) To a solution of compound 18i (1.23 g, 3.46 mmol) in THF (20 mL) cooled in an ice bath was added a solution of NaHCO$_3$ (0.58 g, 6.92 mmol) in water (3 mL) followed by Boc anhydride (0.755 g, 3.46 mmol). After stirring in the ice bath for 2 hours, EtOAc was added. The solution was washed with brine 2×, dried (MgSO$_4$) and concentrated. Column chromatography eluting with 50% EtOAc/hexanes provided the N-Boc product (1.42 g, 90%). MS (M+H)$^+$=456.2.

(18k) A mixture of compound 18j (1.42 g, 3.1 mmol), 4-chloromethyl-2-methylquinoline (0.71 g, 3.1 mmol) and K$_2$CO$_3$ (0.86 g, 6.2 mmol) in DMF (8 mL) was stirred at 80° C. for 2 hours. EtOAc was added. The solution was washed with brine 3×, dried (MgSO$_4$) and concentrated. Column chromatography eluting with 50% EtOAc/hexanes provided the desired product (0.94 g, 50%). MS (M+H)$^+$=611.2.

(18l) A solution of compound 18k (0.94 g, 1.54 mmol) in 50% TFA in CH$_2$Cl$_2$ (10 mL) was stirred at room temperature for 5 hours and concentrated to give the desired product. MS (M+H)$^+$=455.1.

(18m) Compound 18l was converted to a hydroxamic acid following the procedure described in (16 m). MS (M+H)$^+$= 470.2.

Example 19

(2R,3S)-N-Hydroxy-1-methyl-2-[({4-[(2-methyl-4-quinolinyl)methoxy]phenyl}sulfonyl)methyl]-3-piperidinecarboxamide bis(trifluoroacetate)

(19a) Compound 18l was treated with formaldehyde and sodium triacetoxyborohydride following the procedure described in (17a). MS (M+H)$^+$=469.2.

(19b) Compound 19a was converted to a hydroxamic acid following the procedure described in (16 m). MS (M+H)$^+$= 484.2.

Example 20

(2R,3S)-N-Hydroxy-2-[({4-[(2-methyl-4-quinolinyl)methoxy]phenyl}sulfonyl)methyl]-3-pyrrolidinecarboxamide bis(trifluoroacetate)

(20a) Into a solution of 18f (6.5 g, 11.22 mmol) in CH$_2$Cl$_2$ cooled at −78° C. was bubbled oxygen for 10 min and then ozone. Bubbling was continued for 15 more min after the solution turned blue. The solution was flushed with nitrogen until turning clear. Trimethyl phosphite (2.78 mL, 22.45 mmol) was added. The mixture was stirred at room temperature overnight and diluted with $CH_2Cl_2$. The solution was washed with brine 3×, dried ($MgSO_4$) and concentrated. Column chromatography eluting with 40% EtOAc/hexanes provided the aldehyde (4.1 g, 63%). MS $(M+H)^+$=582.

(20b) Compound 20a (4.1 g, 7.56 mmol) in MeOH (200 mL) was hydrogenated at 50 psi for 3 hours using 10% Pd—C (1.5 g) as the catalyst. The catalyst was filtered off and the solution was concentrated to give the pyrrolidine derivative (2.3 g, 90%). MS $(M+H)^+$=342.1.

(20c) To a solution of 20b (2.3 g, 6.74 mmol) in dioxane (9 mL) and water (9 mL) cooled in an ice bath was added Boc anhydride (1.62 g, 7.4 mmol) followed by $NaHCO_3$ (0.84 g, 10 mmol). After stirring for 2 hours, EtOAc was added. The solution was washed with brine 3×, dried ($MgSO_4$) and concentrated. Column chromatography eluting with 40% EtOAc/hexanes provided the Boc-protected product (2.6 g, 87%). MS $(M+H)^+$=442.2.

(20d) A mixture of 20c (2.6 g, 5.89 mmol), 4-chloromethyl-2-methylquinoline hydrochloride (1.61 g, 7.06 mmol) and potassium carbonate (2.03 g, 14.73 mmol) in DMF (12 mL) was stirred at 60° C. for 4 hours. EtOAc was added. The solution was washed with brine 3×, dried ($MgSO_4$) and concentrated. Column chromatography eluting with 40% EtOAc/hexanes provided the desired product (3 g, 85%). MS $(M+H)^+$=597.3.

(20e) A solution of 20d (3 g, 5.03 mmol) in $CH_2Cl_2$ (10 mL) and TFA (10 mL) was stirred at room temperature for 4 hours and concentrated. MS $(M+H)^+$=441.2.

(20f) To a solution of 20e (200 mg, 0.299 mmol) in DMF (2 mL) cooled in an ice bath was added a solution of hydroxylamine hydrochloride (138 mg, 2 mmol) and NMM (303 mg, 3 mmol) in DMF (1 mL) followed PyBOP (208 mg, 0.4 mmol). After stirring for 1 h, the solution was filtered. Purification by reversed phase HPLC provided the hydroxamic acid (120 mg, 59%). MS $(M+H)^+$=456.1.

Example 21

(2R,3S)-N-Hydroxy-1-methyl-2-[({4-[(2-methyl-4-quinolinyl)methoxy]phenyl}sulfonyl)methyl]-3-pyrrolidinecarboxamide bis(trifluoroacetate)

(21a) A mixture of 20e (200 mg, 0.299 mmol), formaldehyde (37% solution in water, 120 mg, 1.5 mmol), sodium triacetoxyborohydride (148 mg, 0.7 mmol) and NMM (202 mg, 2 mmol) in DMF (2 mL) was stirred at room temperature for 2 hours. Purification by reversed phase HPLC provided the N-methyl analog (150 mg, 74%). MS $(M+H)^+$= 455.1.

(21b) To a solution of 21a (150 mg, 0.22 mmol) in DMF (2 mL) cooled at −40° C. was added NMM (101 mg, 1 mmol) followed by propyl chloroformate (62 mg, 0.5 mmol). After stirring at −30 to −40° C. for 30 min, a solution of hydroxylamine hydrochloride (138 mg, 2 mmol) and NMM (202 mg, 2 mmol) in DMF (1 mL) was added. Stirring was continued at −30° C. for 30 min. Purification by reversed phase HPLC provided the hydroxamic acid (110 mg, 72%). MS $(M+H)^+$=470.1.

Example 22 tert-Butyl (3R,4S)-3-[(hydroxyamino)carbonyl]-4-[({4-[(2-methyl-4-quinolinyl)methoxy]phenyl}sulfonyl)methyl]-1-pyrrolidinecarboxylate trifluoroacetate (22a) A solution of N-benzylglycine (12.39 g, 75 mmol), dimethyl maleate (6.26 g, 50 mmol), paraformaldehyde (4.5 g, 150 mmol) and DIEA (8.7 mL, 50 mmol) in toluene (100 mL) was stirred at reflux for 2 hours and concentrated. The residue was taken up in EtOAc. The solution was washed with brine 3×, dried ($MgSO_4$) and concentrated. Column chromatography eluting with 50% EtOAc/hexanes provided dimethyl cis-1-benzyl-3,4-pyrrolidinedicarboxylate (4.8 g, 34%). MS $(M+H)^+$=278.5.

(22b) A solution of 22a (4.8 g, 17.3 mmol), $(Boc)_2O$ (5.66 g, 26 mmol) and DIEA (3 mL, 17.3 mmol) in MeOH (50 mL) was hydrogenated at 55 psi overnight using 20% $Pd(OH)_2$ on carbon as the catalyst. The catalyst was filtered off and the filtrate was concentrated. Column chromatography eluting with 50% EtOAc/hexanes provided the desired product (3.5 g, 71%). MS $(2M+H)^+$=575.3.

(22c) To a solution of 22b (5.6 g, 19.5 mmol) in THF (40 mL) was added a solution of KOH (2.3 g, 40.1 mmol) in water (40 mL) over a period of 1 h. Stirring was continued for another hour. THF was removed in vacuo. After diluting with water (50 mL), the solution was extracted with ether. The water layer was acidified with 1 N HCl (40 mL) at 0° C. and extracted with EtOAc. The organic layer was washed with brine 2×, dried ($MgSO_4$), and concentrated to give the carboxylic acid (4.2 g, 84%) as a solid. MS $(2M-H)^-$=517.2.

(22d) To a solution of 22c (3.91 g, 16.2 mmol) in THF (50 mL) cooled in an ice bath was slowly added $NaBH_4$ (0.61 g, 16.2 mmol) over a period of 20 min. After stirring in the ice bath for 2 hours, the reaction was quenched with aqueous citric acid (20 mL). EtOAc was added. The organic phase was separated, washed with brine 3×, dried ($MgSO_4$) and concentrated. Column chromatography eluting with 50% EtOAc/hexanes provided the lactone product (3 g, 81%). MS $(M+Na+CH_3CN)^+$=291.3.

(22e) To a solution of 4-mercaptophenol (5 g, 40 mmol) in DMF (20 mL) cooled in an ice bath was added NaH (60% dispersion in mineral oil, 1.6 g, 40 mmol). After stirring for 5 min under nitrogen, a solution of 22d (3 g, 13.2 mmol) in DMF (10 mL) was added. The mixture was stirred at 50° C. for 5 hours. EtOAc was added. The solution was washed with citric acid 2×, brine 3×, dried ($MgSO_4$), and concentrated. Column chromatography eluting with 10% MeOH/$CH_2Cl_2$ provided the desired product (3.85 g, 82%),. MS $(2M+H)^+$=707.4.

(22f) To a solution of 22e (3.85 g, 10.9 mmol) and $K_2CO_3$ (1.5 g, 11 mmol) in DMF (10 mL) was added iodomethane (1.537 g, 10.9 mmol) in batches over a period of 1 h. Stirring was continued for another hour. EtOAc was added. The solution was washed with aqueous citric acid 1×, brine 3×, dried ($MgSO_4$) and concentrated. Column chromatography eluting with 50% EtOAc/hexanes provided the methyl ester (1.9 g, 50%). MS $(2M+H)^+$=735.4.

(22g) A mixture of 22f (1.9 g, 5.18 mmol), 4-chloromethyl-2-methylquinoline hydrochloride (1.18 g, 5.18 mmol) and $K_2CO_3$ (1.43 g, 10.36 mmol) in DMF (10 mL) was stirred at 70° C. for 2 hours. EtOAc was added. The solution was washed with brine 3×, dried ($MgSO_4$) and concentrated. Purification on a silica gel column eluting with 50% EtOAc/hexanes provided the desired product (2.6 g, 96%). MS $(M-H)^-$=521.4.

(22h) A mixture of 22g (2.6 g, 4.97 mmol) and Oxone® (6.14 g, 10 mmol) in THF (15 mL), MeOH (10 mL) and water (20 mL) was stirred at room temperature for 2 hours. EtOAc was added. The organic phase was separated, washed with $NaHCO_3$ 1×, brine 3×, dried ($MgSO_4$) and concentrated to give the Oxone® product (2.45 g, 88%). MS $(M+H)^+$=555.2.

(22i) Compound 22h (150 mg, 0.27 mmol) was dissolved in 1.7 M $HONH_2$ solution (3 mL). The solution was stirred at room temperature for 30 min and concentrated. Purification by reversed phase HPLC provided the hydroxamic acid (115 mg, 63%). MS (M+H)$^+$=556.3.

Example 23

(3R,4S)-N-Hydroxy-4-[({4-[(2-methyl-4-quinolinyl)methoxy]phenyl}sulfonyl)methyl]-3-pyrrolidinecarboxamide bis(trifluoroacetate)

Compound 22i was treated with 50% TFA/CH$_2$Cl$_2$ following the procedure described for Example 4 to provide the NH analog. MS (M+H)$^+$=456.2.

Example 24

(3R,4S)-N-Hydroxy-1-isopropyl-4-[({4-[(2-methyl-4-quinolinyl)methoxy]phenyl}sulfonyl)methyl]-3-pyrrolidinecarboxamide bis(trifluoroacetate)

(24a) Compound 22h was treated with 50% TFA/CH$_2$Cl$_2$ for 30 min to give the Boc deprotected product. MS (M+H)$^+$=455.2.

(24b) A mixture of 24a (164 mg, 0.36 mmol), acetone (0.2 mL, 2.7 mmol), Na(OAc)$_3$BH, and DIEA (0.2 mL, 1.14 mmol) in DMF (2 mL) was stirred at 50° C. for 3 hours. Purification by reversed phase HPLC provided the N-isopropyl analog (112 mg, 43%). MS (M+H)$^+$=497.3.

(24c) Compound 24b (110 mg) was dissolved in 1.7 M HONH$_2$ solution (3 mL). After stirring at room temperature for 30 min, the solution was concentrated. Purification by reversed phase HPLC provided the hydroxamic acid (78 mg). MS (M+H)$^+$=498.3.

Example 25

(3R,4S)-N-Hydroxy-4-[({4-[(2-methyl-4-quinolinyl)methoxy]phenyl}sulfonyl)methyl]-1-(2-propynyl)-3-pyrrolidinecarboxamide bis(trifluoroacetate)

(25a) A mixture of compound 24a (164 mg, 0.36 mmol), propargyl bromide (47 mg, 0.4 mmol) and TEA (111 mg, 1.08 mmol) in CH$_2$Cl$_2$ (2 mL) was stirred at room temperature for 5 hours. Purification by reversed phase HPLC provided the N-propargyl analog (42 mg). MS (M+H)$^+$=493.3.

(25b) Compound 25a (40 mg) was dissolved in 1.7 M HONH$_2$ solution (2 mL). After stirring at room temperature for 30 min, the solution was concentrated. Purification by reversed phase HPLC afforded the hydroxamic acid. MS (M+H)$^+$=494.3.

Example 26

(3S,4S)-N-Hydroxy-3-({[4-(3-methoxyphenoxy)phenyl]sulfonyl}methyl)-4-piperidinecarboxamide trifluoroacetate (26a) To a solution of 3e (0.4 g, 1.05 mmol) in THF (3 mL) and MeOH (2 mL) was added a solution of Oxone® (1.29 g, 2.09 mmol) in water (4 mL). The mixture was stirred at room temperature for 2 h. EtOAc was added. The solution was washed with NaHCO$_3$ 1×, brine 2×, dried (MgSO$_4$), and concentrated to give the sulfone derivative (0.41 g, 94%). MS (M+H)$^+$=414.0.

(26b) A mixture of 26a (200 mg, 0.48 mmol), 3-methoxyphenylboronic acid (147 mg, 0.96 mmol), Cu(OAc)$_2$ (96 mg, 0.48 mmol), 4 A molecular sieves (340 mg) and pyridine (0.2 mL, 2.4 mmol) in CH$_2$Cl$_2$ (6 mL) was stirred under ambient atmosphere for 18 h at room temperature and filtered. The filtrate was concentrated. Flash chromatography eluting with 20% EtOAc/hexanes provided the desired product (150 mg, 60%). MS (M+H)$^+$=520.1.

(26c) Compound 26b (150 mg, 0.289 mmol) was dissolved in 1.7 M HONH$_2$ solution (3 mL). After stirring at room temperature for 30 min, AcOH (0.3 mL) was added. The solution was concentrated. Purification by reversed phase HPLC provided the hydroxamic acid. MS (M+H)$^+$=521.1.

(26d) Compound 26c was treated with 50% TFA/CH$_2$Cl$_2$ following the procedure described for Example 4 to furnish the NH analog. MS (M+H)$^+$=421.0.

Example 27

(3S,4S)-3-({[4-(3-Chlorophenoxy)phenyl]sulfonylmethyl)-N-hydroxy-4-piperidinecarboxamide trifluoroacetate This compound was prepared using procedures analogous to those described for Example 26. MS (M+H)$^+$=425.0.

Example 28

(3S, 4S)-N-Hydroxy-3-({[4-(3-methylphenoxy)phenyl]sulfonyl}methyl)-4-piperidinecarboxamide trifluoroacetate This compound was prepared using procedures analogous to those described for Example 26. MS (M+H)$^+$=405.0.

Example 29

(2R, 3S)-N-Hydroxy-1-isopropyl-2-[({4-[(2-methyl-4-quinolinyl)methoxy]phenyl}sulfonyl)methyl]-3-pyrrolidinecarboxamide bis(trifluoroacetate)

This compound was prepared using procedures analogous to those described for Example 21. MS (M+H)$^+$=498.2.

Example 30

(2R, 3S)-N-Hydroxy-2-[({4-[(2-methyl-4-quinolinyl)methoxy]phenyl}sulfonyl)methyl]-1-(methylsulfonyl)-3-pyrrolidinecarboxamide trifluoroacetate (30a) To a stirred solution of 20e (200 mg, 0.294 mmol) in DMF cooled in an ice bath was added triethylamine (202 mg, 2 mmol) followed by methanesulfonyl chloride (56 mg, 0.4 mmol). The mixture was stirred for 1 h in the ice bath and purified by reversed phase HPLC to provide the desired sulfonamide (50 mg, 26%). MS (M+H)$^+$=519.1.

(30b) Compound 30a was converted to a hydroxamic acid using the procedure described in (21b). MS (M+H)$^+$=534.1.

Example 31

(2R, 3S)-1-(2-Furoyl)-N-hydroxy-2-[({4-[(2-methyl-4-quinolinyl)methoxy]phenyl}sulfonyl)methyl]-3-pyrrolidinecarboxamide trifluoroacetate (31a) To a solution of 2-furoic acid (0.56 g, 5 mmol) and N-hydroxysuccinimide (0.69 g, 6 mmol) in THF (10 mL) was added DCC (1.24 g, 6 mmol). The mixture was stirred at room temperature overnight and filtered. The solvent was removed under reduced pressure to provide the activated ester.

(31b) To a stirred solution of 20e (200 mg, 0.294 mmol) and 31a (125 mg, 0.6 mmol) in DMF (2 mL) was added triethylamine (202 mg, 2 mmol). The solution was stirred at room temperature for 1 h. Purification by reversed phase HPLC provided the desired product (150 mg, 79%). MS (M+H)$^+$=535.1.

(31c) Compound 31b was converted to a hydroxamic acid following the procedure described in (21b). MS (M+H)$^+$=550.2.

Example 32

(2R,3S)-1-(3-Furoyl)-N-hydroxy-2-[({4-[(2-methyl-4-quinolinyl)methoxy]phenyl}sulfonyl)methyl]-3-pyrrolidinecarboxamide trifluoroacetate This compound was prepared using procedures analogous to those described for Example 31. MS (M+H)$^+$=550.2.

Example 33

(2R,3S)-N-Hydroxy-2-[({4-[(2-methyl-4-quinolinyl)methoxy]phenyl}sulfonyl)methyl]-1-(tetrahydro-2-furanylcarbonyl)-3-pyrrolidinecarboxamide trifluoroacetate This compound was prepared using procedures analogous to those described for Example 31. MS (M+H)$^+$=554.2.

Example 34

(2R,3S)-N-Hydroxy-2-[({4-[(2-methyl-4-quinolinyl)methoxy]phenyl}sulfonyl)methyl]-1-(tetrahydro-3-furanylcarbonyl)-3-pyrrolidinecarboxamide trifluoroacetate This compound was prepared using procedures analogous to those described for Example 31. MS (M+H)$^+$=554.2.

Example 35

(2R,3S)-1-Acetyl-N-hydroxy-2-[({4-[(2-methyl-4-quinolinyl)methoxy]phenyl}sulfonyl)methyl]-3-pyrrolidinecarboxamide trifluoroacetate This compound was prepared using procedures analogous to those described for Example 31. MS (M+H)$^+$=498.2.

TABLE 1

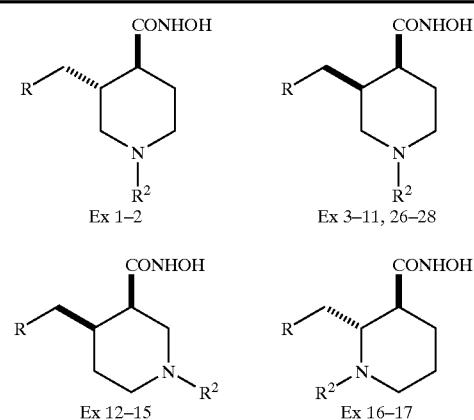

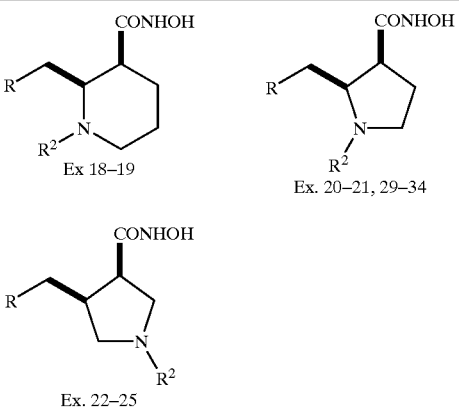

| Ex # | R | R$^2$ | MS (M + H)$^+$ |
|---|---|---|---|
| 1 | [4-[(2-methyl-4-quinolinyl)methoxy]phenyl]sulfonyl | methyl | 484.1 |
| 2 | [4-[(2-methyl-4-quinolinyl)methoxy]phenyl]sulfonyl | isopropyl | 512.1 |
| 3 | [4-[(2-methyl-4-quinolinyl)methoxy]phenyl]sulfonyl | t-butoxy carbonyl | 570.2 |
| 4 | [4-[(2-methyl-4-quinolinyl)methoxy]phenyl]sulfonyl | H | 470.1 |
| 5 | [4-[(2-methyl-4-quinolinyl)methoxy]phenyl]sulfonyl | methyl | 484.1 |
| 6 | [4-[(2-methyl-4-quinolinyl)methoxy]phenyl]sulfonyl | isopropyl | 512.1 |
| 7 | [4-[(2-methyl-4-quinolinyl)methoxy]phenyl]sulfonyl | n-propyl | 512.1 |
| 8 | [4-[(2-methyl-4-quinolinyl)methoxy]phenyl]sulfonyl | n-butyl | 526.2 |
| 9 | [4-[(2-methyl-4-quinolinyl)methoxy]phenyl]sulfonyl | isobutyl | 526.2 |
| 10 | [4-[(2-methyl-4-quinolinyl)methoxy]phenyl]sulfonyl | propargyl | 508.1 |
| 11 | [4-[(2-methyl-4-quinolinyl)methoxy]phenyl]sulfonyl | allyl | 510.1 |
| 12 | [4-[(2-methyl-4-quinolinyl)methoxy]phenyl]sulfonyl | t-butoxy carbonyl | 570.2 |
| 13 | [4-[(2-methyl-4-quinolinyl)methoxy]phenyl]sulfonyl | H | 470.1 |
| 14 | [4-[(2-methyl-4-quinolinyl)methoxy]phenyl]sulfonyl | methyl | 484.1 |
| 15 | [4-[(2-methyl-4-quinolinyl)methoxy]phenyl]sulfonyl | isopropyl | 512.1 |
| 16 | [4-[(2-methyl-4-quinolinyl)methoxy]phenyl]sulfonyl | H | 470.2 |
| 17 | [4-[(2-methyl-4-quinolinyl)methoxy]phenyl]sulfonyl | methyl | 484.2 |
| 18 | [4-[(2-methyl-4-quinolinyl)methoxy]phenyl]sulfonyl | H | 470.2 |
| 19 | [4-[(2-methyl-4-quinolinyl)methoxy]phenyl]sulfonyl | methyl | 484.2 |
| 20 | [4-[(2-methyl-4-quinolinyl)methoxy]phenyl]sulfonyl | H | 456.1 |
| 21 | [4-[(2-methyl-4-quinolinyl)methoxy]phenyl]sulfonyl | methyl | 470.1 |
| 22 | [4-[(2-methyl-4-quinolinyl)methoxy]phenyl]sulfonyl | t-butoxy carbonyl | 556.3 |
| 23 | [4-[(2-methyl-4-quinolinyl)methoxy]phenyl]sulfonyl | H | 456.2 |
| 24 | [4-[(2-methyl-4-quinolinyl)methoxy]phenyl]sulfonyl | isopropyl | 498.3 |
| 25 | [4-[(2-methyl-4-quinolinyl)methoxy]phenyl]sulfonyl | propargyl | 494.3 |
| 26 | [4-[(3-methoxyphenyl)oxy]phenyl]sulfonyl | H | 421.0 |
| 27 | [4-[(3-chlorophenyl)oxy]phenyl]sulfonyl | H | 425.0 |
| 28 | [4-[(3-methylphenyl)oxy]phenyl]sulfonyl | H | 405.0 |

TABLE 1-continued

| # | | | |
|---|---|---|---|
| 29 | [4-[(2-methyl-4-quinolinyl)methoxy]phenyl]sulfonyl | isopropyl | 498.2 |
| 30 | [4-[(2-methyl-4-quinolinyl)methoxy]phenyl]sulfonyl | methanesulfonyl | 534.1 |
| 31 | [4-[(2-methyl-4-quinolinyl)methoxy]phenyl]sulfonyl | 2-furoyl | 550.2 |
| 32 | [4-[(2-methyl-4-quinolinyl)methoxy]phenyl]sulfonyl | 3-furoyl | 550.2 |
| 33 | [4-[(2-methyl-4-quinolinyl)methoxy]phenyl]sulfonyl | tetrahydro-2-furanylcarbonyl | 554.2 |
| 34 | [4-[(2-methyl-4-quinolinyl)methoxy]phenyl]sulfonyl | tetrahydro-3-furanylcarbonyl | 554.2 |
| 35 | [4-[(2-methyl-4-quinolinyl)methoxy]phenyl]sulfonyl | acetyl | 498.2 |

The following tables contain representative examples of the present invention. Each entry in each table is intended to be paired with each formula at the start of the table.

TABLE 2

| Entry # | $R^{10}$ |
|---|---|
| 1 | H |
| 2 | methyl |

TABLE 2-continued

| | |
|---|---|
| 3 | methoxy |
| 4 | ethoxy |
| 5 | propyloxy |
| 6 | isopropyloxy |
| 7 | isobutyloxy |
| 8 | t-butyloxy |
| 9 | cyclopropyloxy |
| 10 | cyclobutoxy |
| 11 | cyclopentyloxy |
| 12 | cyclohexyloxy |
| 13 | phenyloxy |
| 14 | 3,5-dimethylphenyloxy |
| 15 | 3,5-dichlorophenyloxy |
| 16 | 3-methylphenyloxy |
| 17 | 3-chlorophenyloxy |
| 18 | 4-methylphenyloxy |
| 19 | 4-chlorophenyloxy |
| 20 | 4-pyridyloxy |
| 21 | 2,6-dimethylpyridyloxy |
| 22 | 4-quinolinyloxy |
| 23 | 5-quinolinyloxy |
| 24 | 6-quinolinyloxy |
| 25 | 5-isoquinolinyloxy |
| 26 | 2-methyl-4-quinolinyloxy |
| 27 | phenylmethoxy |
| 28 | (3,5-dimethylphenyl)methoxy |
| 29 | (3,5-dichlorophenyl)methoxy |
| 30 | (3,5-dimethoxyphenyl)methoxy |
| 31 | (3,5-dibromophenyl)methoxy |
| 32 | [3,5-bis(trifluoromethyl)phenyl]methoxy |
| 33 | (2-pyridinyl)methoxy |
| 34 | (3-pyridinyl)methoxy |
| 35 | (4-pyridinyl)methoxy |
| 36 | (2,6-dimethyl-4-pyridinyl)methoxy |
| 37 | (2-chloro-6-methyl-4-pyridinyl)methoxy |
| 38 | (2-chloro-6-methoxy-4-pyridinyl)methoxy |
| 39 | (4-quinolinyl)methoxy |
| 40 | (5-quinolinyl)methoxy |
| 41 | (6-quinolinyl)methoxy |
| 42 | (5-isoquinolinyl)methoxy |
| 43 | (2-methyl-4-quinolinyl)methoxy |
| 44 | (2-methoxy-4-quinolinyl)methoxy |
| 45 | (2-amino-4-quinolinyl)methoxy |
| 46 | (4-quinolinyl)ethoxy |
| 47 | (5-quinolinyl)ethoxy |
| 48 | (6-quinolinyl)ethoxy |
| 49 | (5-isoquinolinyl)ethoxy |
| 50 | (2-methyl-4-quinolinyl)ethoxy |
| 51 | (2-methoxy-4-quinolinyl)ethoxy |
| 52 | (2-amino-4-quinolinyl)ethoxy |
| 53 | phenyloxymethyl |
| 54 | (3,5-dimethylphenyl)oxymethyl |
| 55 | (3,5-dichlorophenyl)oxymethyl |
| 56 | [3,5-bis(trifluoromethyl)phenyl]oxymethyl |
| 57 | 4-pyridnyloxymethyl |
| 58 | (2,6-dimethylpyridinyl)oxymethyl |
| 59 | (2-chloro-6-methyl-4-pyridinyl)oxymethyl |
| 60 | (2-chloro-6-methoxy-4-pyridinyl)oxymethyl |
| 61 | 4-quinolinyloxymethyl |
| 62 | 5-quinolinyloxymethyl |
| 63 | 6-pyridinyloxymethyl |
| 64 | 5-isoquinolinyloxymethyl |
| 65 | (2-methyl-4-quinolinyl)oxymethyl |
| 66 | 5-indolyloxy |
| 67 | 1-methyl-5-indolyloxy |
| 68 | 1-ethyl-5-indolyloxy |
| 69 | 5-indolyloxymethyl |
| 70 | (1-methyl-5-indolyl)oxymethyl |
| 71 | (1-ethyl-5-indolyl)oxymethyl |
| 72 | 5-indolylmethoxy |
| 73 | (1-methyl-5-indolyl)methoxy |
| 74 | (1-ethyl-5-indolyl)methoxy |
| 75 | (1-benzimidazolyl)methyl |
| 76 | (1-benzimidazolyl)ethyl |
| 77 | (1,2,3-benzotriazol-1-yl)methyl |
| 78 | (1,2,3-benzotriazol-1-yl)ethyl |
| 79 | (2,5-dimethyl-4-thiazolyl)methyoxy |
| 80 | (2,4-dimethyl-5-thiazolyl)methoxy |
| 81 | (4,5-dimethyl-2-thiazolyl)methoxy |
| 82 | (2-isopropyl-4-thiazolyl)methoxy |
| 83 | (2-isopropyl-5-thiazolyl)methoxy |
| 84 | (3,5-dimethyl-4-isoxazolyl)methoxy |
| 85 | 2-butynyloxy |
| 86 | 2-pentynyloxy |

TABLE 3

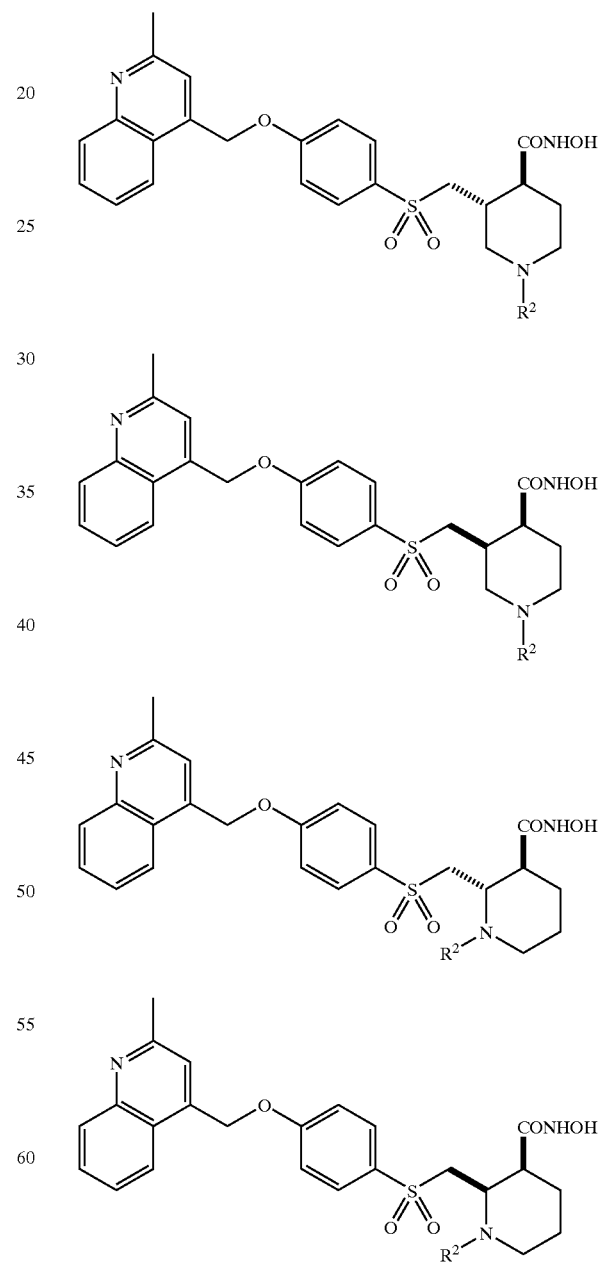

TABLE 3-continued

[Structure: 2-methylquinoline-4-CH2-O-C6H4-SO2-CH2-(piperidine with CONHOH at 3-position, N-R2)]

[Structure: 2-methylquinoline-4-CH2-O-C6H4-SO2-CH2-(piperidine with CONHOH at 3-position, N-R2)]

[Structure: 2-methylquinoline-4-CH2-O-C6H4-SO2-CH2-(pyrrolidine with CONHOH at 3-position, N-R2)]

[Structure: 2-methylquinoline-4-CH2-O-C6H4-SO2-CH2-(pyrrolidine with CONHOH at 3-position, N-R2)]

| Entry # | R² |
|---|---|
| 1 | H |
| 2 | methyl |
| 3 | ethyl |
| 4 | n-propyl |
| 5 | n-butyl |
| 6 | 1-methylethyl |
| 7 | 2-methylpropyl |
| 8 | cyclobutyl |
| 9 | cyclopentyl |
| 10 | cyclohexyl |
| 11 | allyl |
| 12 | propargyl |
| 13 | phenylmethyl |
| 14 | 2-pyridinylmethyl |
| 15 | 3-pyridinylmethyl |
| 16 | 4-pyridinylmethyl |
| 17 | acetyl |
| 18 | propionyl |
| 19 | butyryl |
| 20 | 2-methyl-propionyl |
| 21 | 2,2-dimethylpropionyl |
| 22 | 2-pyridinylcarbonyl |
| 23 | 3-pyridinylcarbonyl |
| 24 | 4-pyridinylcarbonyl |
| 25 | methanesulfonyl |
| 26 | benzenesulfonyl |
| 27 | 2-pyridinylsulfonyl |
| 28 | 3-pyridinylsulfonyl |
| 29 | 4-pyridinylsulfonyl |
| 30 | methoxycarbonyl |
| 31 | propyloxycarbonyl |
| 32 | 1-methylethoxycarbonyl |
| 33 | methylaminocarbonyl |
| 34 | propylaminocarbonyl |
| 35 | 2-methylethylaminocarbonyl |
| 36 | 2,2-dimethylethylaminocarbonyl |
| 37 | 2-pyridinylaminocarbonyl |
| 38 | 3-pyridinylaminocarbonyl |
| 39 | 4-pyridinylaminocarbonyl |

UTILITY

The compounds of formula I are expected to possess matrix metalloprotease and/or aggrecanase and/or TNF-αinhibitory activity. The MMP inhibitory activity of the compounds of the present invention is demonstrated using assays of MMP activity, for example, using the assay described below for assaying inhibitors of MMP activity. The compounds of the present invention are expected to be bioavailable in vivo as demonstrated, for example, using the ex vivo assay described below. The compounds of formula I are expected to have the ability to suppress/inhibit cartilage degradation in vivo, for example, as demonstrated using the animal model of acute cartilage degradation described below.

The compounds provided by this invention should also be useful as standards and reagents in determining the ability of a potential pharmaceutical to inhibit MPs. These would be provided in commercial kits comprising a compound of this invention.

Metalloproteases have also been implicated in the degradation of basement membranes to allow infiltration of cancer cells into the circulation and subsequent penetration into other tissues leading to tumor metastasis (Stetler-Stevenson, Cancer and Metastasis Reviews, 9, 289–303, 1990). The compounds of the present invention should be useful for the prevention and treatment of invasive tumors by inhibition of this aspect of metastasis.

The compounds of the present invention should also have utility for the prevention and treatment of osteopenia associated with matrix metalloprotease-mediated breakdown of cartilage and bone that occurs in osteoporosis patients.

Compounds that inhibit the production or action of TNF and/or Aggrecanase and/or MP's are potentially useful for the treatment or prophylaxis of various inflammatory, infectious, immunological or malignant diseases. These include, but are not limited to Cachexia includes cachexia resulting from cancer, HIV, congestive heart failure (CHF), and any chronic disease. Rheumatoid arthritis includes early, juvenile (including juvenile chronic arthritis), and adult rheumatoid arthritis. Shock includes septic and haemodynamic shock. Spondylitis includes ankylosing spondiylitis. Cachexia includes cachexia resulting from cancer, HIV, congestive heart failure (CHF), and any chronic disease. Rheumatoid arthritis includes early, juvenile (including juvenile chronic arthritis), and adult rheumatoid arthritis. Shock includes septic and haemodynamic shock. Spondylitis includes ankylosing spondiylitis.

Some compounds of the present invention have been shown to inhibit TNF production in lipopolysacharride stimulated mice, for example, using the assay for TNF induction in mice and in human whole blood as described below.

Some compounds of the present invention have been shown to inhibit aggrecanase, a key enzyme in cartilage breakdown, as determined by the aggrecanase assay described below.

As used herein "$\mu$g" denotes microgram, "mg" denotes milligram, "g" denotes gram, "$\mu$L" denotes microliter, "mL" denotes milliliter, "L" denotes liter, "nM" denotes nanomolar, "$\mu$M" denotes micromolar, "mM" denotes millimolar, "M" denotes molar and "nm" denotes nanometer. "Sigma" stands for the Sigma-Aldrich Corp. of St. Louis, Mo.

A compound is considered to be active if it has an $IC_{50}$ or $K_i$ value of less than about 10 $\mu$M for the inhibition of a desired MP. Preferred compounds of the present invention have $K_i$'s or $IC_{50}$'s of $\leq 1$, $\mu$M. More preferred compounds of the present invention have $K_i$'s or $IC_{50}$'s of $\leq 0.1$ $\mu$M. Even more preferred compounds of the present invention have $K_i$'s or $IC_{50}$'s of $\leq 0.01$, $\mu$M. Still more preferred compounds of the present invention have $K_i$'s or $IC_{50}$'s of $\leq 0.001$, $\mu$M.

Aggrecanase Enzymatic Assay

A novel enzymatic assay was developed to detect potential inhibitors of aggrecanase. The assay uses active aggrecanase accumulated in media from stimulated bovine nasal cartilage (BNC) or related cartilage sources and purified cartilage aggrecan monomer or a fragment thereof as a substrate.

The substrate concentration, amount of aggrecanases time of incubation and amount of product loaded for Western analysis were optimized for use of this assay in screening putative aggrecanase inhibitors. Aggrecanase is generated by stimulation of cartilage slices with interleukin-1 (IL-1), tumor necrosis factor alpha (TNF-$\alpha$) or other stimuli. Matrix metalloproteases (MMPs) are secreted from cartilage in an inactive, zymogen form following stimulation, although active enzymes are present within the matrix. We have shown that following depletion of the extracellular aggrecan matrix, active MMPs are released into the culture media (Tortorella, M. D. et. al. Trans. Ortho. Res. Soc. 1995, 20, 341). Therefore, in order to accumulate BNC aggrecanase in culture media, cartilage is first depleted of endogenous aggrecan by stimulation with 500 ng/ml human recombinant IL-$\beta$ for 6 days with media changes every 2 days. Cartilage is then stimulated for an additional 8 days without media change to allow accumulation of soluble, active aggrecanase in the culture media. In order to decrease the amount of other matrix metalloproteases released into the media during aggrecanase accumulation, agents that inhibit MMP-1,-2,-3, and -9 biosynthesis are included during stimulation. This BNC conditioned media, containing aggrecanase activity is then used as the source of aggrecanase for the assay. Aggrecanase enzymatic activity is detected by monitoring production of aggrecan fragments produced exclusively by cleavage at the Glu373-Ala374 bond within the aggrecan core protein by Western analysis using the monoclonal antibody, BC-3 (Hughes, C E, et al., Biochem J 306:799–804, 1995). This antibody recognizes aggrecan fragments with the N-terminus, 374ARGSVIL, generated upon cleavage by aggrecanase. The BC-3 antibody recognizes this neoepitope only when it is at the N-terminus and not when it is present internally within aggrecan fragments or within the aggrecan protein core. Other proteases produced by cartilage in response to IL-1 do not cleave aggrecan at the Glu373-Ala374 aggrecanase site; therefore, only products produced upon cleavage by aggrecanase are detected. Kinetic studies using this assay yield a Km of 1.5+/–0.35 $\mu$M for aggrecanase.

To evaluate inhibition of aggrecanase, compounds are prepared as 10 mM stocks in DMSO, water or other solvents and diluted to appropriate concentrations in water. Drug (50 uL) is added to 50 uL of aggrecanase-containing media and 50 uL of 2 mg/ml aggrecan substrate and brought to a final volume of 200 uL in 0.2 M Tris, pH 7.6, containing 0.4 M NaCl and 40 mM $CaCl_2$. The assay is run for 4 hr at 37° C., quenched with 20 mM EDTA and analyzed for aggrecanase-generated products. A sample containing enzyme and substrate without drug is included as a positive control and enzyme incubated in the absence of substrate serves as a measure of background.

Removal of the glycosaminoglycan side chains from aggrecan is necessary for the BC-3 antibody to recognize the ARGSVIL epitope on the core protein. Therefore, for analysis of aggrecan fragments generated by cleavage at the Glu373-Ala374 site, proteoglycans and proteoglycan fragments are enzymatically deglycosylated with chondroitinase ABC (0.1 units/10 ug GAG) for 2 hr at 37° C. and then with keratanase (0.1 units/10 ug GAG) and keratanase II (0.002 units/10 ug GAG) for 2 hr at 37° C. in buffer containing 50 mM sodium acetate, 0.1 M Tris/HCl, pH 6.5. After digestion, aggrecan in the samples is precipitated with 5 volumes of acetone and resuspended in 30 ul of Tris glycine SDS sample buffer (Novex) containing 2.5% beta mercaptoethanol. Samples are loaded and then separated by SDS-PAGE under reducing conditions with 4–12% gradient gels, transferred to nitrocellulose and immunolocated with 1:500 dilution of antibody BC3. Subsequently, membranes are incubated with a 1:5000 dilution of goat anti-mouse IgG alkaline phosphatase second antibody and aggrecan catabolites visualized by incubation with appropriate substrate for 10–30 minutes to achieve optimal color development. Blots are quantitated by scanning densitometry and inhibition of aggrecanase determined by comparing the amount of product produced in the presence versus absence of compound.

PBMC ASSAY

Human peripheral blood mononuclear cells (PBMC) were obtained from normal donor blood by leukophoresis and isolated by Ficoll-Paque density separation. PBMCs were suspended in 0.5ml RPMI 1640 with no serum at $2\times10^6$ cells/ml in 96 well polystyrene plates. Cells were preincubated 10 minutes with compound, then stimulated with 1 $\mu$g/ml LPS (Lipopolysaccharide, Salmonella typhimurium) to induce TNF production. After an incubation of 5 hours at 37° C. in 95% air, 5% $CO_2$ environment, culture supernatants were removed and tested by standard sandwich ELISA for TNF production.

TNF Human Whole Blood Assay

Blood is drawn from normal donors into tubes containing 143 USP units of heparin/10 mL. 225 ul of blood is plated directly into sterile polypropylene tubes. Compounds are diluted in DMSO/serum free media and added to the blood samples so the final concentration of compounds are 50, 10, 5, 1, 0.5, 0.1, and 0.01 $\mu$M. The final concentration of DMSO does not exceed 0.5%. Compounds are preincubated for 15 minutes before the addition of 10 ng/ml LPS. Plates are incubated for 5 hours in an atmosphere of 5% $CO_2$ in air. At the end of 5 hours, 750 uL of serum free media is added to each tube and the samples are spun at 1200RPM for 10 minutes. The supernatant is collected off the top and assayed for TNF-alpha production by a standard sandwich ELISA.

The ability of compounds to inhibit TNF-alpha production by 50% compared to DMSO treated cultures is given by the IC50 value.

TNF Induction In Mice

Test compounds are administered to mice either I.P. or P.O. at time zero. Immediately following compound administration, mice receive an I.P. injection of 20 mg of D-galactosamine plus 10 μg of lipopolysaccharide. One hour later, animals are anesthetized and bled by cardiac puncture. Blood plasma is evaluated for TNF levels by an ELISA specific for mouse TNF. Administration of representative compounds of the present invention to mice results in a dose-dependent suppression of plasma TNF levels at one hour in the above assay.

MMP Counterscreens

The enzymatic activities of recombinant MMP-1, 2, 3, 9, and 13 were measured at 25° C. with a fluorometric assay (Copeland, R. A.; Lombardo, D.; Giannaras, J. and Decicco, C. P. *Bioorganic Med. Chem. Lett.* 1995, 5, 1947–1952). Final enzyme concentrations in the assay were between 0.05 and 10 nM depending on the enzyme and the potency of the inhibitor tested. The permisive peptide substrate, MCA-Pro-Leu-Gly-Leu-DPA-Ala-Arg-$NH_2$, was present at a final concentration of 10 uM in all assays. Initial velocities, in the presence or absence of inhibitor, were measured as slopes of the linear portion of the product progress curves. IC50 values were determined by plotting the inhibitor concentration dependence of the fractional velocity for each enzyme, and fitting the data by non-linear least squares methods to the standard isotherm equation (Copeland, R. A. Enzymes: *A practical Introduction to Structure, Mechanism and Data Analysis*, Wiley-VHC, New York, 1996, pp 187–223). All of the compounds studied here were assumed to act as competitive inhibitors of the enzyme, binding to the active site Zn atom as previously demonstrated by crystallographic studies of MMP-3 complexed with related hydroxamic acids (Rockwell, A.; Melden, M.; Copeland, R. A.; Hardman, K.; Decicco, C. P. and DeGrado, W. F. *J. Am. Chem. Soc.* 1996, 118, 10337–10338). Based on the assumption of competitive inhibiton, the IC50 values were converted to $K_i$ values as previously described.

Compounds tested in the above assay are considered to be active if they exhibit a $K_i$ of $\leq 10$ μM. Preferred compounds of the present invention have $K_i$'s of $\leq 1$ μM. More preferred compounds of the present invention have $K_i$'s of $\leq 0.1$ μM. Even more preferred compounds of the present invention have $K_i$'s of $\leq 0.01$ μM. Still more preferred compounds of the present invention have $K_i$'s of $\leq 0.001$ μM.

Using the methodology described above, a number of compounds of the present invention were found to exhibit $K_i$'s of $\leq 10$ μM, thereby confirming the utility of the compounds of the present invention.

Dosage and Formulation

The compounds of the present invention can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is Remington's Pharmaceutical Sciences, Mack Publishing.

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed as an antiinflammatory and antiarthritic agent.

The compounds of this invention can be administered by any means that produces contact of the active agent with the agent's site of action in the body of a mammal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration; the renal and hepatic function of the patient; and the effect desired. An ordinarily skilled physician or veterinarian can readily determine and prescribe the effective amount of the drug required to prevent, counter, or arrest the progress of the condition.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. For a normal male adult human of approximately 70 kg of body weight, this translates into a dosage of 70 to 1400 mg/day. Intravenously, the most preferred doses will range from about 1 to about 10 mg/kg/minute during a constant rate infusion. Advantageously, compounds of the present invention may be administered in a single daily dose, or the total daily dosage may be administered in divided doses of two, three, or four times daily.

The compounds for the present invention can be administered in intranasal form via topical use of suitable intranasal vehicles, or via transdermal routes, using those forms of transdermal skin patches wall known to those of ordinary skill in that art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition. The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water-soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field. Useful pharmaceutical dosage-forms for administration of the compounds of this invention can be illustrated as follows:

Capsules

Capsules are prepared by conventional procedures so that the dosage unit is 500 milligrams of active ingredient, 100 milligrams of cellulose and 10 milligrams of magnesium stearate.

A large number of unit capsules may also prepared by filling standard two-piece hard gelatin capsules each with 100 milligrams of powdered active ingredient, 150 milligrams of lactose, 50 milligrams of cellulose, and 6 milligrams magnesium stearate.

| Syrup | |
| --- | --- |
| | Wt. % |
| Active Ingredient | 10 |
| Liquid Sugar | 50 |
| Sorbitol | 20 |
| Glycerine | 5 |
| Flavor, Colorant and Preservative | as required |
| Water | as required |

The final volume is brought up to 100% by the addition of distilled water.

| Aqueous Suspension | |
| --- | --- |
| | Wt. % |
| Active Ingredient | 10 |
| Sodium Saccharin | 0.01 |
| Keltrol ® (Food Grade Xanthan Gum) | 0.2 |
| Liquid Sugar | 5 |
| Flavor, Colorant and Preservative | as required |
| Water | as required |

Xanthan gum is slowly added into distilled water before adding the active ingredient and the rest of the formulation ingredients. The final suspension is passed through a homogenizer to assure the elegance of the final products.

| Resuspendable Powder | |
| --- | --- |
| | Wt. % |
| Active Ingredient | 50.0 |
| Lactose | 35.0 |
| Sugar | 10.0 |
| Acacia | 4.7 |
| Sodium Carboxylmethylcellulose | 0.3 |

Each ingredient is finely pulverized and then uniformly mixed together. Alternatively, the powder can be prepared as a suspension and then spray dried.

Semi-Solid Gel

| | Wt. % |
|---|---|
| Active Ingredient | 10 |
| Sodium Saccharin | 0.02 |
| Gelatin | 2 |
| Flavor, Colorant and Preservative | as required |
| Water | as required |

Gelatin is prepared in hot water. The finely pulverized active ingredient is suspended in the gelatin solution and then the rest of the ingredients are mixed in. The suspension is filled into a suitable packaging container and cooled down to form the gel.

Semi-Solid Paste

| | Wt. % |
|---|---|
| Active Ingredient | 10 |
| Gelcarin ® (Carrageenin gum) | 1 |
| Sodium Saccharin | 0.01 |
| Gelatin | 2 |
| Flavor, Colorant and Preservative | as required |
| Water | as required |

Gelcarin® is dissolved in hot water (around 80° C.) and then the fine-powder active ingredient is suspended in this solution. Sodium saccharin and the rest of the formulation ingredients are added to the suspension while it is still warm. The suspension is homogenized and then filled into suitable containers.

Emulsifiable Paste

| | Wt. % |
|---|---|
| Active Ingredient | 30 |
| Tween ® 80 and Span ® 80 | 6 |
| Keltrol ® | 0.5 |
| Mineral Oil | 63.5 |

All the ingredients are carefully mixed together to make a homogenous paste.

Soft Gelatin Capsules

A mixture of active ingredient in a digestable oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

Tablets may be prepared by conventional procedures so that the dosage unit is 500 milligrams of active ingredient, 150 milligrams of lactose, 50 milligrams of cellulose and 10 milligrams of magnesium stearate.

A large number of tablets may also be prepared by conventional procedures so that the dosage unit was 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is made isotonic with sodium chloride and sterilized.

Suspension

An aqueous suspension is prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

The compounds of the present invention may be administered in combination with a second therapeutic agent, especially non-steroidal anti-inflammatory drugs (NSAID's). The compound of Formula I and such second therapeutic agent can be administered separately or as a physical combination in a single dosage unit, in any dosage form and by various routes of administration, as described above.

The compound of Formula I may be formulated together with the second therapeutic agent in a single dosage unit (that is, combined together in one capsule, tablet, powder, or liquid, etc.). When the compound of Formula I and the second therapeutic agent are not formulated together in a single dosage unit, the compound of Formula I and the second therapeutic agent may be administered essentially at the same time, or in any order; for example the compound of Formula I may be administered first, followed by administration of the second agent. When not administered at the same time, preferably the administration of the compound of Formula I and the second therapeutic agent occurs less than about one hour apart, more preferably less than about 5 to 30 minutes apart.

Preferably the route of administration of the compound of Formula I is oral. Although it is preferable that the compound of Formula I and the second therapeutic agent are both administered by the same route (that is, for example, both orally), if desired, they may each be administered by different routes and in different dosage forms (that is, for example, one component of the combination product may be administered orally, and another component may be administered intravenously).

The dosage of the compound of Formula I when administered alone or in combination with a second therapeutic agent may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a sustained-release material that effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The present invention also includes pharmaceutical kits useful, for example, in the treatment or prevention of osteoarthritis or rheumatoid arthritis, which comprise one or more containers containing a pharmaceutical composition comprising a therapeutically effective amount of a compound of Formula I. Such kits may further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, may also be included in the kit.

In the present disclosure it should be understood that the specified materials and conditions are important in practicing the invention but that unspecified materials and conditions are not excluded so long as they do not prevent the benefits of the invention from being realized.

Although this invention has been described with respect to specific embodiments, the details of these embodiments are not to be construed as limitations. Various equivalents, changes, and modifications may be made without departing from the spirit and scope of this invention, and it is understood that such equivalent embodiments are part of this invention.

What is claimed is:

1. A compound of formula I:

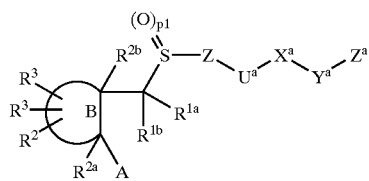

I or a stereoisomer or pharmaceutically acceptable salt form thereof, wherein;

A is CONHOH, ring B is a 5 membered heterocyclic ring consisting of: 4 carbon atoms, 0–1 carbonyl groups 0–2 double bonds, and 1 heteroatom selected from N—, and $NR^2$, provided that N—$R^2$ forms other than an N—O, N—N, or N—S bond;

Z is phenyl substituted with 0–5 $R^b$;

$U^a$ is O, $NR^{a1}$, or C(O);

$X^a$ is methylene;

$Y^a$ is absent or is selected from O, $NR^{a1}$, $S(O)_p$, and C(O);

$Z^a$ is quinoline substituted with 0–5 $R^c$;

$R^{1a}$ is selected from H, $C_{1-4}$ alkyl, phenyl, benzyl, $CH_2OR^3$, and $CH_2NR^aR^{a1}$;

$R^{1b}$ is selected from H, $C_{1-4}$ alkyl, phenyl, benzyl, $CH_2OR^3$, and $CH_2NR^aR^{a1}$;

$R^2$ is selected from Q, $C_{1-10}$ alkylene-Q substituted with 0–3 $R^{b1}$, $C_{2-10}$ alkenylene-Q substituted with 0–3 $R^{b1}$, $C_{2-10}$ alkynylene-Q substituted with 0–3 $R^{b1}$, $(CR^aR^{a1})_{r1}O(CR^aR^{a1})_r$-Q,$(CR^aR^{a1})_{r1}NR^a(CR^aR^{a1})_r$-Q, $(CR^aR^{a1})_{r1}C(O)(CR^aR^{a1})_r$-Q,$(CR^aR^{a1})_{r1}C(O)O(CR^aR^{a1})_r$-Q, $(CR^aR^{a1})_{r1}OC(O)(CR^aR^{a1})_r$-Q, $(CR^aR^{a1})_{r1}C(O)NR^aR^{a1}$, $(CR^aR^{a1})_{r1}C(O)NR^a(CR^aR^{a1})_r$-Q,$(CR^aR^{a1})_{r1}NR^aC(O)(CR^aR^{a1})_r$-Q, $(CR^aR^{a1})_{r1}OC(O)O(CR^aR^{a1})_r$-Q,$(CR^aR^{a1})_{r1}OC(O)NR^a(CR^aR^{a1})_r$-Q, $(CR^aR^{a1})_{r1}NR^aC(O)O(CR^aR^{a1})_r$-Q, $(CR^aR^{a1})_{r1}NR^aC(O)NR^a(CR^aR^{a1})_{r1}$-Q, $(CR^aR^{a1})_{r1}S(O)_p(CR^aR^{a1})_r$-Q,$(CR^aR^{a1})_{r1}SO_2NR^a(CR^aR^{a1})_r$-Q, $(CR^aR^{a1})_{r1}NR^aSO_2(CR^aR^{a1})_r$-Q, and $(CR^aR^{a1})_{r1}NR^aSO_2NR^a(CR^aR^{a1})_r$-Q;

$R^{2a}$ is H, $R^{2b}$ is H;

Q is selected from H, a $C_{3-13}$ carbocycle substituted with 0–5 Rd and a 5–14 membered heterocycle consisting of: carbon atoms and 1–4 heteroatoms selected from the group consisting of N, O, and $S(O)_p$, and substituted with 0–5 Rd;

$R^3$, at each occurrence, is selected from $Q^1$, $C_{1-6}$ alkylene-$Q^1$, $C_{2-6}$ alkenylene-$Q^1$, $C_{2-6}$ alkynylene-$Q^1$, $(CR^aR^{a1})_{r1}O(CH_2)_r$-$Q^1$, $(CR^aR^{a1})_{r1}NR^a(CR^aR^{a1})_r$-$Q^1$, $(CR^aR^{a1})_{r1}NR^aC(O)(CR^aR^{a1})_r$-$Q^1$, $(CR^aR^{a1})_{r1}C(O)NR^a(CR^aR^{a1})_r$-$Q^1$, $(CR^aR^{a1})_{r1}C(O)(CR^aR^{a1})_r$-$Q^1$, $(CR^aR^{a1})_{r1}C(O)O(CR^aR^{a1})_r$-$Q^1$, $(CR^aR^{a1}_2)_{r1}S(O)_p(CR^aR^{a1})_r$-$Q^1$ and $(CR^aR^{a1})_{r1}SO_2NR^a(CR^aR^{a1})_r$-$Q^1$;

alternatively, when two $R^3$s are attached to the same carbon atom, they combine to form a 3–8 membered carbocyclic or heterocyclic ring consisting of: carbon atoms and 0–3 heteroatoms selected from the group consisting of N, O, and $S(O)_p$, and substituted with 0–3 Rd;

$Q^1$ is selected from H, phenyl substituted with 0–3 Rd, naphthyl substituted with 0–3 Rd and a 5–10 membered heteroaryl consisting of: carbon atoms and 1–4 heteroatoms selected from the group consisting of N, O, and $S(O)_p$, and substituted with 0–3 Rd;

$R^a$, at each occurrence, is independently selected from H, $C_{1-4}$ alkyl, phenyl and benzyl;

$R^{a1}$, at each occurrence, is independently selected from H and $C_{1-4}$ alkyl;

alternatively, $R^a$ and $R^{a1}$ when attached to a nitrogen are taken together with the nitrogen to which they are attached to form a 5 or 6 membered ring comprising carbon atoms and from 0–1 additional heteroatoms selected from the group consisting of N, O, and $S(O)_p$;

$R^{a2}$, at each occurrence, is independently selected from $C_{1-4}$ alkyl, phenyl and benzyl;

$R^b$, at each occurrence, is independently selected from $C_{1-6}$alkyl, $OR^a$, Cl, F, Br, I, =O, —CN, $NO_2$, $NR^aR^{a1}$, $C(O)R^a$, $C(O)OR^a$, $C(O)NR^aR^{a1}$, $RaNC(O)NR^aR^{a1}$, $OC(O)NR^aR^{a1}$, $R^aNC(O)O$, $S(O)_2NR^aR^{a1}$, $NR^aS(O)_2R^{a2}$, $NR^aS(O)_2NR^aR^{a1}$, $OS(O)_2NR^aR^{a1}$, $NR^aS(O)_2R^{a2}$, $S(O)_pR^{a2}$, $CF_3$, and $CF_2CF_3$;

$R^{b1}$, at each occurrence, is independently selected from $OR^a$, Cl, F, Br, I, =O, —CN, $NO_2$, and $NR^aR^{a1}$;

$R^c$, at each occurrence, is independently selected from $C_{1-6}$ alkyl, $OR^a$, Cl, F, Br, I, =O, —CN, $NO_2$, $NR^aR^{a1}$, $C(O)R^a$, $C(O)OR^a$, $C(O)NR^aR^{Ra1}$, $R^aNC(O)NR^aR^{a1}$, $OC(O)NR^aR^{a1}$, $R^aNC(O)O$, $S(O)_2NR^aR^{a1}$, $NR^aS(O)_2R^{a2}$, $NR^aS(O)_2NR^aR^{a1}$, $OS(O)_2NR^aR^{a1}$, $NR^aS(O)_2R^{a2}$, $S(O)_pR^{a2}$, $CF_3$, $CF_2CF_3$, $C_{3-10}$ carbocycle and a 5–14 membered heterocycle consisting of: carbon atoms and 1–4 heteroatoms selected from the group consisting of N, O, and $S(O)_p$;

$R^d$, at each occurrence, is independently selected from $C_{1-6}$ alkyl, $OR^a$, Cl, F, Br, I, =O, —CN, $NO_2$, $NR^aR^{a1}$, $C(O)R^a$, $C(O)OR^a$, $C(O)NR^aR^{a1}$, $R^aNC(O)NR^aR^{a1}$, $OC(O)NR^aR^{a1}$, $R^aNC(O)O$, $S(O)_2NR^aR^{a1}$, $NR^aS(O)_2R^{a2}$, $NR^aS(O)_2NR^aR^{a1}$, $OS(O)_2NR^aR^{a1}$, $NR^aS(O)_2R^{a2}$, $S(O)_pR^{a2}$, $CF_3$, $CF_2CF_3$, $C_{3-10}$ carbocycle and a 5–14 membered heterocycle consisting of: carbon atoms and 1–4 heteroatoms selected from the group consisting of N, O, and $S(O)_p$;

p, at each occurrence, is selected from 0, 1, and 2;

p1 is 0, 1, or 2;

r, at each occurrence, is selected from 0, 1, 2, 3, and 4; and, r1, at each occurrence, is selected from 0, 1, 2, 3, and 4.

2. A compound according to claim 1, wherein the compound is of formula II:

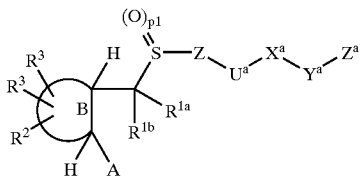

II or a stereoisomer or pharmaceutically acceptable salt form thereof, wherein;

Z is phenyl substituted with 0–4 $R^b$;

$Y^a$ is absent or is selected from O and $NR^{a1}$;

$R^2$ is selected from Q, $C_{1-6}$ alkylene-Q, $C_{2-6}$ alkenylene-Q, $C_{2-6}$ alkynylene-Q, $(CR^aR^{a1})_{r1}O(CR^aR^{a1})_r$-Q, $(CR^aR^{a1})_{r1}NR^a(CR^aR^{a1})_r$-Q, $(CR^aR^{a1})_{r1}C(O)(CR^aR^{a1})_r$-Q, $(CR^aR^{a1})_{r1}C(O)O(CR^aR^{a1})_r$-Q, $(CR^aR^{a1})_rC(O)NR^aR^{a1}$, $(CR^aR^{a1})_{r1}C(O)NR^a(CR^aR^{a1})_r$-Q, $(CR^aR^{a1})_{r1}S(O)(CR^aR^{a1})_r$-Q, and $(CR^aR^{a1})_{r1}SO_2NR^a(CR^aR^{a1})_r$-Q;

Q is selected from H, a $C_{3-6}$ carbocycle substituted with 0–5 Rd, and a 5–10 membered heterocycle consisting of: carbon atoms and 1–4 heteroatoms selected from the group consisting of N, O, and $S(O)_p$, and substituted with 0–5 Rd;

$R^a$, at each occurrence, is independently selected from H, $C_{1-4}$ alkyl, phenyl and benzyl;

$R^{a1}$, at each occurrence, is independently selected from H and $C_{1-4}$ alkyl;

alternatively, $R^a$ and $R^{a1}$ when attached to a nitrogen are taken together with the nitrogen to which they are attached to form a 5 or 6 membered ring comprising carbon atoms and from 0–1 additional heteroatoms selected from the group consisting of N, O, and $S(O)_p$;

$R^{a2}$, at each occurrence, is independently selected from $C_{1-4}$ alkyl, phenyl and benzyl;

$R^b$, at each occurrence, is independently selected from $C_{1-6}$ alkyl, $OR^a$, Cl, F, Br, =O, —CN, $NR^aR^{a1}$, $C(O)R^a$, $C(O)OR^a$, $C(O)NR^aR^{a1}$, $S(O)_2NR^aR^{a1}$, $S(O)_pR^{a2}$, and $CF_3$;

$R^c$, at each occurrence, is independently selected from $C_{1-6}$ alkyl, $OR^a$, Cl, F, Br, =O, —CN, $NR^aR^{a1}$, $C(O)R^a$, $C(O)OR^a$, $C(O)NR^aR^{a1}$, $S(O)_2NR^aR^{a1}$, $S(O)_pR^{a2}$, $CF^3$, $C_{3-6}$ carbocycle and a 5–6 membered heterocycle consisting of: carbon atoms and 1–4 heteroatoms selected from the group consisting of N, O, and $S(O)_p$; and $R^d$, at each occurrence, is independently selected from $C_{1-6}$ alkyl, $OR^a$, Cl, F, Br, =O, —CN, $NR^aR^{a1}$, $C(O)R^a$, $C(O)OR^a$, $C(O)NR^aR^{a1}$, $S(O)_2NR^aR^{a1}$, $S(O)_pR^{a2}$, $CF_3$, $C_{3-6}$ carbocycle and a 5–6 membered heterocycle consisting of: carbon atoms and 1–4 heteroatoms selected from the group consisting of N, O, and $S(O)_p$.

3. A compound according to claim 2, wherein the compound is of formula III:

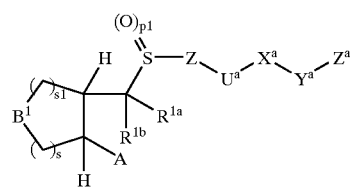

III or a stereoisomer or pharmaceutically acceptable salt form thereof, wherein;

$B^1$ is $NR^2$, provided that $N—R^2$ forms other than an N—O, N—N, or N—S bond;

Z is phenyl substituted with 0–3 $R^b$;

$Y^a$ is absent or is selected from O and $NR^{a1}$;

$Z^a$ quinoline substituted with 0–3 $R^c$;

$R^2$ is selected from Q, $C_{1-6}$ alkylene-Q, $C_{2-6}$ alkenylene-Q, $C_{2-6}$ alkynylene-Q, $(CR^aR^{a1})_{r1}O(CR^aR^{a1})_r$-Q, $(CR^aR^{a1})_{r1}NR^a(CR^aR^{a1})_r$-Q, $(CR^aR^{a1})_{r1}C(O)(CR^aR_{a1})_r$-Q, $(CR^aR^{a1})_{r1}C(O)O(CR^aR^{a1})_r$-Q, $(CR^aR^{a2})_{r1}C(O)NR^aR^{a1}$, $(CR^aR^{a2})_{r1}C(O)NR^a(CR^aR^{a1})_r$-Q, and $(CR^aR^{a1})_{r1}S(O)_p(CR^aR^{a1})_r$-Q;

Q is selected from H, a $C_{3-6}$ carbocycle substituted with 0–3 $R^d$ and a 5–10 membered heterocycle consisting of: carbon atoms and 1–4 heteroatoms selected from the group consisting of N, O, and $S(O)_p$, and substituted with 0–3 $R^d$;

$R^a$, at each occurrence, is independently selected from H, $C_{1-4}$ alkyl, phenyl and benzyl;

$R^{a1}$, at each occurrence, is independently selected from H and $C_{1-4}$ alkyl;

$R^{a2}$, at each occurrence, is independently selected from $C_{1-4}$ alkyl, phenyl and benzyl;

$R^b$, at each occurrence, is independently selected from $C_{1-4}$ alkyl, $OR^a$, Cl, F, =O, $NR^aR^{a1}$, $C(O)R^a$, $C(O)OR^a$, $C(O)NR^aR^{a1}$, $S(O)_2NR^aR^{a1}$, $S(O)_pR^{a2}$, and $CF_3$;

$R^c$, at each occurrence, is independently selected from $C_{1-6}$ alkyl, $OR^a$, Cl, F, Br, =O, $NR^aR^{a1}$, $C(O)R^a$, $C(O)NR^aR^{a1}$, $S(O)_2NR^aR^{a1}$, $S(O)_pR^{a2}$, and $CF_3$;

$R^d$, at each occurrence, is independently selected from $C_{1-6}$ alkyl, $OR^a$, Cl, F, Br, =O, $NR^aR^{a1}$, $C(O)R^a$, $C(O)NR^aR^{a1}$, $S(O)_2NR^aR^{a1}$, $S(O)_pR^{a2}$, $CF_3$ and phenyl; and s and s1 combine to total 1, 2, 3, or 4.

4. A compound according to claim 3, wherein the compound is of formula IV:

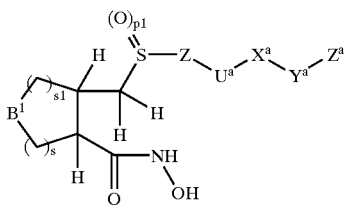

or a stereoisomer or pharmaceutically acceptable salt form thereof, wherein;

$U^a$ is absent or is O;

$Y^a$ is absent or is O;

$R^2$ is selected from Q, $C_{1-6}$ alkylene-Q, $C_{2-6}$ alkynylene-Q, $(CR^aR^{a1})_{r1}O(CR^aR^{a1})_r$-Q, $(CR^aR^{a1})_{r1}NR^a(CR^aR^{a1})_r$-Q, $C(O)(CR^aR^{a1})_r$-Q, $C(O)O(CR^aR^{a1})_r$-Q, $C(O)NR^a(CR^aR^{a1})_r$-Q, and $S(O)_p(CR^aR^{a1})_r$-Q;

Q is selected from H, cyclopropyl substituted with 0–1 $R^d$, cyclobutyl substituted with 0–1 $R^d$, cyclopentyl substituted with 0–1 $R^d$, cyclohexyl substituted with 0–1 $R^d$, phenyl substituted with 0–2 Rd and a heteroaryl substituted with 0–3 $R^d$, wherein the heteroaryl is selected from pyridyl, quinolinyl, thiazolyl, furanyl, imidazolyl, and isoxazolyl;

$R^a$, at each occurrence, is independently selected from H, $CH_3$, and $CH_2CH_3$;

$R^{a1}$, at each occurrence, is independently selected from H, $CH_3$, and $CH_2CH_3$;

$R^{a2}$, at each occurrence, is independently selected from H, $CH_3$, and $CH_2CH_3$;

$R^b$, at each occurrence, is independently selected from $C_{1-4}$ alkyl, $OR^a$, Cl, F, =O, $NR^aR^{a1}$, $C(O)R^a$, $C(O)OR^a$, $C(O)NR^aR^{a1}$, $S(O)_2NR^aR^{a1}$, $S(O)_pR^{a2}$, and $CF_3$;

$R^c$, at each occurrence, is independently selected from $C_{1-6}$ alkyl, $OR^a$, Cl, F, Br, =O, $NR^aR^{a1}$, $C(O)R^a$, $C(O)NR^aR^{a1}$, $S(O)_2NR^aR^{a1}$, $S(O)_pR^{a2}$, and $CF_3$;

$R^d$, at each occurrence, is independently selected from $C_{1-6}$ alkyl, $OR^a$, Cl, F, Br, =O, $NR^aR^{a1}$, $C(O)R^a$, $C(O)NR^aR^{a1}$, $S(O)_2NR^aR^{a1}$, $S(O)_pR^{a2}$, $CF_3$ and phenyl; and s and s1 combine to total 2, 3, or 4.

5. A compound according to claim 1, wherein the compound is selected from the group:

(2R,3S)-N-hydroxy-1-methyl-2-[({4-[(2-methyl-4-quinolinyl)methoxy]phenyl}sulfonyl)methyl]-3-pyrrolidinecarboxamide;

tert-butyl (3R,4S)-3-[(hydroxyamino)carbonyl]-4-[({4-[(2-methyl-4-quinolinyl)methoxy]phenyl}sulfonyl)methyl]-1-pyrrolidinecarboxylate;

(3R,4S)-N-hydroxy-4-[({4-[(2-methyl-4-quinolinyl)methoxy]phenyl}sulfonyl)methyl]-3-pyrrolidinecarboxamide;

(3R,4S)-N-hydroxy-1-isopropyl-4-[({4-[(2-methyl-4-quinolinyl)methoxy]phenyl}sulfonyl)methyl]-3-pyrrolidinecarboxamide;

(3R,4S)-N-hydroxy-4-[({4-[(2-methyl-4-quinolinyl)methoxy]phenyl}sulfonyl)methyl]-1-(2-propynyl)-3-pyrrolidinecarboxamide;

(2R,3S)-N-hydroxy-1-isopropyl-2-[({4-[(2-methyl-4-quinolinyl)methoxy]phenyl}sulfonyl)methyl]-3-pyrrolidinecarboxamide;

(2R,3S)-N-hydroxy-2-[({4-[(2-methyl-4-quinolinyl)methoxy]phenyl}sulfonyl)methyl]-1-(methylsulfonyl)-3-pyrrolidinecarboxamide;

(2R,3S)-1-(2-furoyl)-N-hydroxy-2-[({4-[(2-methyl-4-quinolinyl)methoxy]phenyl}sulfonyl)methyl]-3-pyrrolidinecarboxamide;

(2R,3S)-1-(3-furoyl)-N-hydroxy-2-[({4-[(2-methyl-4-quinolinyl)methoxy]phenyl}sulfonyl)methyl]-3-pyrrolidinecarboxamide;

(2R,3S)-N-hydroxy-2-[({4-[(2-methyl-4-quinolinyl)methoxy]phenyl}sulfonyl)methyl]-1-(tetrahydro-2-furanylcarbonyl)-3-pyrrolidinecarboxamide;

(2R,3S)-N-hydroxy-2-[({4-[(2-methyl-4-quinolinyl)methoxy]phenyl}sulfonyl)methyl]-1-(tetrahydro-3-furanylcarbonyl)-3-pyrrolidinecarboxamide; and;

(2R,3S)-1-acetyl-N-hydroxy-2-[({4-[(2-methyl-4-quinolinyl)methoxy]phenyl}sulfonyl)methyl]-3-pyrrolidinecarboxamide;

or a pharmaceutically acceptable salt form thereof.

6. A pharmaceutical composition, comprising: a pharmaceutically acceptable carrier and a therapeutically effective amount of a compound according to claim 1 or a pharmaceutically acceptable salt form thereof.

7. A method for treating an inflammatory disorder, comprising: administering to a patient in need thereof a therapeutically effective amount of a compound according to claim 1 or a pharmaceutically acceptable salt form thereof.

8. A method, comprising: administering a compound of claim 1 or a pharmaceutically acceptable salt form thereof in an amount effective to treat an inflammatory disorder.

9. A method of treating a condition or disease mediated by MMPs, TNF, aggrecanase, or a combination thereof in a mammal, comprising: administering to the mammal in need of such treatment a therapeutically effective amount of a compound according to claim 1 or a pharmaceutically acceptable salt form thereof.

10. A method of treating according to claim 9, wherein the disease or condition is referred to as acute infection, acute phase response, age related macular degeneration, alcoholism, allergy, allergic asthma, aneurism, anorexia, aortic aneurism, asthma, athersclerosis, atopic dermatitis, autoimmune disease, autoimmune hepatitis, Bechet's disease, cachexia, calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pulmonary emphysema, pydoderma gangrenosum, relapsing polychondritis, Reiter's syndrome, rheumatic fever, rheumatoid arthritis, sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

11. A pharmaceutical composition, comprising: a pharmaceutically acceptable carrier and a therapeutically effective amount of a compound according to claim 2 or a pharmaceutically acceptable salt form thereof.

12. A pharmaceutical composition, comprising: a pharmaceutically acceptable carrier and a therapeutically effective amount of a compound according to claim 3 or a pharmaceutically acceptable salt form thereof.

13. A pharmaceutical composition, comprising: a pharmaceutically acceptable carrier and a therapeutically effective amount of a compound according to claim 4 or a pharmaceutically acceptable salt form thereof.

14. A pharmaceutical composition, comprising: a pharmaceutically acceptable carrier and a therapeutically effective amount of a compound according to claim 5 or a pharmaceutically acceptable salt form thereof.

15. A method for treating an inflammatory disorder, comprising: administering to a patient in need thereof a therapeutically effective amount of a compound according to claim 2 or a pharmaceutically acceptable salt form thereof.

16. A method for treating an inflammatory disorder, comprising: administering to a patient in need thereof a therapeutically effective amount of a compound according to claim 3 or a pharmaceutically acceptable salt form thereof.

17. A method for treating an inflammatory disorder, comprising: administering to a patient in need thereof a therapeutically effective amount of a compound according to claim 4 or a pharmaceutically acceptable salt form thereof.

18. A method for treating an inflammatory disorder, comprising: administering to a patient in need thereof a therapeutically effective amount of a compound according to claim 5 or a pharmaceutically acceptable salt form thereof.

19. A method, comprising: administering a compound of claim 2 or a pharmaceutically acceptable salt form thereof in an amount effective to treat an inflammatory disorder.

20. A method, comprising: administering a compound of claim 3 or a pharmaceutically acceptable salt form thereof in an amount effective to treat an inflammatory disorder.

21. A method, comprising: administering a compound of claim 4 or a pharmaceutically acceptable salt form thereof in an amount effective to treat an inflammatory disorder.

22. A method, comprising: administering a compound of claim 5 or a pharmaceutically acceptable salt form thereof in an amount effective to treat an inflammatory disorder.

23. A method of treating a condition or disease mediated by MMPs, TNF, aggrecanase, or a combination thereof in a mammal, comprising: administering to the mammal in need of such treatment a therapeutically effective amount of a compound according to claim 2 or a pharmaceutically acceptable salt form thereof.

24. A method of treating a condition or disease mediated by MMPs, TNF, aggrecanase, or a combination thereof in a mammal, comprising: administering to the mammal in need of such treatment a therapeutically effective amount of a compound according to claim 3 or a pharmaceutically acceptable salt form thereof.

25. A method of treating a condition or disease mediated by MMPs, TNF, aggrecanase, or a combination thereof in a mammal, comprising: administering to the mammal in need of such treatment a therapeutically effective amount of a compound according to claim 4 or a pharmaceutically acceptable salt form thereof.

26. A method of treating a condition or disease mediated by MMPs, TNF, aggrecanase, or a combination thereof in a mammal, comprising: administering to the mammal in need of such treatment a therapeutically effective amount of a compound according to claim 5 or a pharmaceutically acceptable salt form thereof.

27. A method of treating according to claim 23, wherein the disease or condition is referred to as acute infection, acute phase response, age related macular degeneration, alcoholism, allergy, allergic asthma, aneurism, anorexia, aortic aneurism, asthma, athersclerosis, atopic dermatitis, autoimmune disease, autoimmune hepatitis, Bechet's disease, cachexia, calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pulmonary emphysema, pydoderma gangrenosum, relapsing polychondritis, Reiter's syndrome, rheumatic fever, rheumatoid arthritis, sarcoidosis, scieroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

28. A method of treating according to claim 24, wherein the disease or condition is referred to as acute infection, acute phase response, age related macular degeneration, alcoholism, allergy, allergic asthma, aneurism, anorexia, aortic aneurism, asthma, athersclerosis, atopic dermatitis, autoimmune disease, autoimmune hepatitis, Bechet's disease, cachexia, calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pulmonary emphysema, pydoderma gangrenosum, relapsing polychondritis, Reiter's syndrome, rheumatic fever, rheumatoid arthritis, sarcoidosis, scieroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

29. A method of treating according to claim 25, wherein the disease or condition is referred to as acute infection, acute phase response, age related macular degeneration, alcoholism, allergy, allergic asthma, aneurism, anorexia, aortic aneurism, asthma, athersclerosis, atopic dermatitis, autoimmune disease, autoimmune hepatitis, Bechet's disease, cachexia, calcium pyrophosphate dihydrate deposition disease, cardiovascular effects, chronic fatigue syndrome, chronic obstruction pulmonary disease, coagulation, congestive heart failure, comeal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pulmonary emphysema, pydoderma gangrenosum, relapsing polychondritis, Reiter's syndrome, rheumatic fever, rheumatoid arthritis, sarcoidosis, scleroderma, sepsis syndrome, Still's disease, shock, Siogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

30. A method of treating according to claim 26, wherein the disease or condition is referred to as acute infection, acute phase response, age related macular degeneration, alcoholism, allergy, allergic asthma, aneurism, anorexia, aortic aneurism, asthma, athersclerosis, atopic dermatitis, autoimmune disease, autoimmune hepatitis, Bechet's disease, cachexia, calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pulmonary emphysema, pydoderma gangrenosum, relapsing polychondritis, Reiter's syndrome, rheumatic fever, rheumatoid arthritis, sarcoidosis, scieroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

* * * * *